United States Patent [19]

Ikeda et al.

[11] Patent Number: 5,200,628

[45] Date of Patent: Apr. 6, 1993

[54] METHOD FOR DISTINGUISHING PARTICLES IN FLUID AND APPARATUS FOR THE SAME INCLUDING PLURAL SENSORS AND WEIGHTING

[75] Inventors: Teruo Ikeda; Masao Watanabe, both of Yokohama, Japan

[73] Assignee: Nikuni Machinery Industrial Co., Ltd., Kawasaki, Japan

[21] Appl. No.: 827,983

[22] Filed: Jan. 29, 1992

Related U.S. Application Data

[62] Division of Ser. No. 610,948, Nov. 9, 1990.

[30] Foreign Application Priority Data

| | | |
|---|---|---|
| Nov. 10, 1989 [JP] | Japan | 1-292568 |
| Sep. 18, 1990 [JP] | Japan | 2-247865 |
| Sep. 18, 1990 [JP] | Japan | 2-247866 |

[51] Int. Cl.⁵ .......................................... G01N 15/06
[52] U.S. Cl. ................................. 250/574; 250/577; 356/343
[58] Field of Search ............... 250/573, 574, 575, 577, 250/208.2, 208.3, 214 R; 356/335, 336, 342, 343

[56] References Cited

U.S. PATENT DOCUMENTS

| | | | |
|---|---|---|---|
| 4,265,535 | 5/1981 | Pitt | 250/575 |
| 4,793,706 | 12/1988 | Caillag et al. | 356/335 |
| 4,999,514 | 3/1991 | Silveston | 356/343 |

Primary Examiner—David C. Nelms
Attorney, Agent, or Firm—Spencer, Frank & Schneider

[57] ABSTRACT

A method of and an apparatus for determining the individual existence of first and second groups of particles contained in a fluid and differing in characteristics from each other that are capable of, e.g., during an automatized ion exchange operation, individually distinguishing anionic and cationic ion-exchange resin particles and capable of easily monitoring their regeneration state. A plurality of beams comprising different wavelength bands are emitted from light-emitting elements, projected onto a subject of measurement containing first and second particles, and received by light-receiving elements, and the reflectivities of the beams are measured. When the ratio of the reflectivity of a first of the beams to that of a second of the beams is above a predetermined value, the subject of measurement is determined to contain particles of the first kind, whereas when that ratio in reflectivity is below the predetermined value, the subject of measurement is determined to contain particles of the second kind.

16 Claims, 18 Drawing Sheets

METHOD FOR DISTINGUISHING PARTICLES IN FLUID AND APPARATUS FOR THE SAME INCLUDING PLURAL SENSORS AND WEIGHTING

This is a division of application Ser. No. 07/610,948 filed Nov. 9, 1990.

BACKGROUND OF THE INVENTION

1. Field of the Invention

The present invention relates to a method of and an apparatus for determining the individual existence of a first group of particles contained in a fluid and a second group of particles in the same fluid but with characteristics different from the first particles. More specifically, the present invention relates to a method and an apparatus capable of distinguishing particles in a fluid that can be advantageously adopted as a method and an apparatus for, for example, distinguishing ion exchange resins used in the purification of water to produce highly pure water, or monitoring the state of such ion exchange resins during their regeneration.

2. Related Art

Ion exchange is performed to produce highly pure water which is required, in great amounts, by facilities such as thermal power plants, nuclear power plants and large, semiconductor-manufacturing plants. In general, an ion exchange operation conducted for this purpose comprises exchange and reduction which are repeatedly performed. A reduction includes backwashing, separation, regeneration, and washing, which take place in the mentioned order.

Such an ion exchange operation may be performed using a mixed-bed deionizer which is advantageous in that the desalted water is both highly pure and neutral and that silicates dissolved in the fluid can be completely removed. In this case, the conventional practice is such that a strongly acidic resin (positive ion exchange resin) and a strongly basic resin (negative ion exchange resin) are charged into a single ion exchange tank. When the resins are evenly mixed together with the aid of air, it is possible to obtain innumerable combinations of the positive ion exchange resin (hereinafter referred to as "cations") and the negative ion exchange resin (hereinafter referred to as "anions"), thereby enabling the production of highly pure desalted water. The two types of resin particles, which move according to Stokes' Law, differ from each other in specific gravity, and this difference results in different sedimentation velocities. Utilizing this fact, backwashing is effected to separate the two types of resins from each other. The separated resins are then regenerated.

An example of a mixed-bed deionizer is shown in FIG. 8. An ion exchange tank 10 contains anions and cations. A first solution 15 comprising sodium hydroxide (caustic soda) is used to regenerate anions, while a second solution 16 comprising hydrochloric acid or sulphuric acid is used to regenerate cations.

FIGS. 9 (a) through 9 (g) show an example of the operation of a mixed-bed deionizer. FIG. 9 (a) shows desalting, FIG. 9 (b) shows backwashing and separation, FIG. 9 (c) shows regeneration of anions, FIG. 9 (d) shows regeneration of cations, FIG. 9 (e) shows washing, FIG. 9 (f) shows mixing, and FIG. 9 (g) shows initialization. These processes are performed in the same order in which they are shown in FIGS. 9 (a) to (g), and cyclically so that an initialization process, in FIG. 9 (g), is followed by a subsequent desalting, in FIG. 9 (a).

In FIGS. 9 (a) to 9 (g), the hatching with lines declining rightward shows regions where anions exist, the hatching with lines declining leftward shows regions where cations exist, and the hatching with criss-cross lines show regions where anions and cations are mixed together.

When the above-described ion exchange operation is being performed, various valves through which water and necessary chemical solutions are introduced into the tank are manually operated to adjust flow rates, whereby the position of the boundaries between the water, the anions and the cations, being visually monitored, is brought to the correct position.

A drawback of a conventional ion exchange operation is that, because valves are manually operated while the state of the ion exchange resins in the tank is visually observed, the operation inevitably requires human labor.

To automatize an ion exchange operation, it is necessary to automatize the valve adjustment for determining flow rates as well as the detection of the state of ion exchange resins. Although the valve adjustment can be automatized with conventional techniques, it is difficult to automatize the detection of the ion exchange resin state with conventional optical sensors or video cameras. This is for the following reasons: particles of ion exchange resins vary in size; particles are distributed in water or solutions at different densities; and it is difficult, in general, to distinguish cations and anions from each other because, although they can be correctly distinguished when they are new, distinguishing them from each other becomes difficult as time passes after their first use because clad deposits on and adheres to the surfaces of the resin particles and thus changes the reflectivity of the resin particle surfaces.

SUMMARY OF THE INVENTION

A primary object of the present invention is to provide a method of and an apparatus for determining the individual existence of a first group of particles contained in a fluid and a second group of particles in the same fluid but with characteristics different from the first particles.

A more specific object of the present invention is to eliminate the above-described drawback of the prior art and provide a method and an apparatus designed to distinguish particles in a fluid that can be adopted as a method and apparatus necessary to, e.g., the automatization of an ion exchange operation, capable of distinguishing from one another the region solely occupied by water (or solution), the anions and the cations, all in an ion exchange tank, and capable of distinctly detecting the existence of the anions and cations.

Another object of the present invention is to provide an apparatus for distinguishing particles in a fluid that can be adopted as a particle distinguishing apparatus necessary to, e.g., an ion exchanging operation and capable of easily monitoring the position of the boundary in an ion exchange tank between the region solely occupied by the water (or a solution) and the ion exchange resins as well as the position of the boundary in the tank between the anions and cations.

Still another object of the present invention is to provide an apparatus for distinguishing particles in a fluid that can be adopted as a particle distinguishing apparatus such as that described above which is also characterized by automatic calibration by means for distinguishing particles.

A further object of the present invention is to provide an apparatus for distinguishing particles in a fluid that can be adopted as a particle distinguishing apparatus capable of exhibiting high reliability by maintaining its dust-proof, water-proof and air-tight characteristics at high levels.

A still further object of the present invention is to provide a method for distinguishing particles in a fluid that is, even when there are slight errors in the output of individual sensors, capable of determining a boundary at which a significant change occurs, as a whole, in the values indicating a certain characteristic of the subject.

A still further object of the present invention is to provide a method for distinguishing particles in a fluid that is capable of quickly and correctly determining the position of a boundary while preventing errors in the boundary determination due to errors in the output of individual sensors.

A still further object of the present invention is to provide a method for distinguishing particles in a fluid that is capable of, when required, easily and automatically correcting characteristics of individual sensors without hindering the entire operation.

In order to achieve the aforesaid objects of the present invention, a first aspect of the present invention provides a method of determining the individual existence of a first group of particles contained in a fluid and a second group of particles in the same fluid but with characteristics different from the first particles that is capable of distinguishing particles in a fluid, the method comprising the steps of: measuring the reflectivities of a plurality of beams comprising different wavelength bands and being projected onto a subject of measurement containing first and second groups of particles; determining that said subject of measurement contains a first group of particles when the ratio of the reflectivity of a first of the beams to the reflectivity of a second of the beams is above a predetermined value; and determining that said subject of measurement contains a second group of particles when the ratio of the reflectivity of the first beam to the reflectivity of the second beam is below said predetermined value.

A method embodying the above-specified method for distinguishing particles according to the present invention may be a method of determining the individual existence of anions and cations contained in a liquid. A plurality of beams comprising different wavelength bands are projected onto a subject of measurement, and the reflectivities of the beams are measured. When the ratio of a first of the beams to a second of the beams is above a predetermined value, it is determined that the subject of measurement contains anions, whereas when the ratio of the first beam to the second beam is below a predetermined value, it is determined that the subject of measurement contains cations.

According to a second aspect of the present invention, there is provided an apparatus for determining the individual existence of a first group of particles contained in a fluid and a second group of particles in the same fluid but with characteristics different from the first particles, the apparatus being capable of distinguishing particles in a fluid, the apparatus comprising: means for measuring the reflectivities of a plurality of beams comprising different wavelength bands, said reflectivity measuring means including light-emitting elements for emitting the beams which are then projected onto a subject of measurement containing particles belonging to either of first and second groups, and light-receiving elements for receiving the light reflected from said subject of measurement; particle distinguishing means which, when the ratio of the reflectivity of a first of the beams to the reflectivity of a second of the beams is above a predetermined value, determines that said subject of measurement contains a first group of particles, whereas when the ratio of the reflectivity of the first beam to the reflectivity of the second beam is below said predetermined value, said particle distinguishing means determines that said subject of measurement contains a second group of particles; and a display for displaying the result of the determination of said particle distinguishing means.

An apparatus embodying the above-specified apparatus for distinguishing particles according to the present invention may be an apparatus for determining the individual existence of anions and cations contained in a liquid. The apparatus uses a plurality of beams comprising different wavelength bands which are emitted from a set of light-emitting elements, projected onto a subject of measurement, reflected from the subject, and received by a set of light-receiving elements. A reflectivity measuring means measures the reflectivities of the beams. When the ratio of a first of the beams to a second of the beams is above a predetermined value, an ion exchange resin distinguishing means determines that the subject of measurement contains anions. When the ratio of the first beam to the second beam is below a predetermined value, the ion exchange resin distinguishing means determines that the subject of measurement contains cations. A display displays the result of the determination of the distinguishing means.

In a preferred embodiment, a plurality of light-receiving elements are vertically arranged on a transparent, flat-plate-shaped wall portion of a tank accommodating the subject of measurement, and a means is provided for detecting, on the basis of an output of the reflectivity measuring means, the position of the boundary between that portion of said subject which is solely composed of a fluid and the groups of particles, as well as the boundary between the anions and the cations. The boundary position detecting means is included in a part of the particle distinguishing means.

The particle distinguishing means also includes a means for calibrating sensitivity degrees and color standards for each of the beams to be used.

The light-emitting elements of the reflectivity measuring means are disposed in such a manner that the light-receiving elements receive only those rays of the beams emitted from the light-emitting elements which are obliquely incident upon the front flat surface of the wall portion of the associated tank.

The apparatus further comprises sealing means which, when the apparatus is mounted on the ion exchange tank, air-tightly seals a structure accommodating at least the reflectivity measuring means In a preferred embodiment of the above-specified method of determining the individual existence of a first group of particles contained in a fluid and a second group of particles in the same fluid but with characteristics different from the first particles that is capable of distinguishing particles in a fluid, the position of a boundary that is indicated by a change in characteristic value is determined by using a plurality of sensors, effecting a predetermined weighting of each of the measurement values output from a plurality of mutually adjacent sensors along all the sensors, obtaining a plurality of weighted values from the weighted measurement values, and comparing the weighted values with one another.

In another preferred embodiment of the above-specified method, the position of a boundary that is indicated by a change in characteristic value is determined by obtaining a plurality of first mean values each resulting from an averaging of the measurement values output from a plurality of mutually adjacent sensors, obtaining a second mean value resulting from an averaging of adjacent ones of the first mean values, repeating the aforesaid averaging until nth (n being an integer at least equal to two) mean values are obtained, and comparing the nth mean values of the same dimension with one another.

In still another preferred embodiment of the above-specified method, the position of a boundary that is indicated by a change in characteristic value is determined by obtaining a plurality of first weighted mean values each resulting from a predetermined weighting of and then an averaging of the measurement values output from a plurality of mutually adjacent sensors, obtaining a plurality of second weighted mean values each resulting from a different weighting of and then an averaging of adjacent ones of said first weighted mean values, repeating the aforesaid steps until mth (m being an integer at least equal to two) weighted mean values are obtained, and comparing the mth weighted mean values with one another.

In any of the above-described preferred embodiments of the method, the measurement values output from the plurality of sensors are divided into a plurality of groups each comprising measurement values from a plurality of mutually adjacent sensors and enabling a mean value of these measurement values to be calculated, and the calculated mean values are examined to check whether or not there is any in-group or inter-group change indicating the position of a boundary.

In determining the position of a boundary, a range possibly containing a change indicating a boundary position is successively narrowed by dividing the measurement values of the sensors into a plurality of groups, comparing the mean values of the groups with one another, and repeating the aforesaid steps a plurality of times in such a manner that, each time the steps are executed, the number of the measurement values belonging to one group from which a mean value is calculated is different, the number of the measurement values in one group being largest in the first execution of the steps and thereafter decreasing in a plurality of successive stages.

In still another embodiment of the above-specified method, a mean value of the measurement values of a group of sensors comprising a plurality of mutually adjacent sensors is compared with each of the measurement values used to obtain the mean value, and, if the ratio expressing the result of the comparison falls outside a predetermined range of the ratio, it is determined that there is an error in the characteristics of the sensor which has output the particular measurement value. On the basis of both the measurement value of the sensor determined to be erroneous and the mean value, a value with which the particular measurement value should be corrected is calculated, and the calculated value is stored as a correction value in a storage. In the subsequent measurements, the measurement values output from the sensor determined to be erroneous are corrected using the correction value stored in the storage.

In this embodiment, the above-described measurement values of the group of the sensors from which the mean value is calculated consist of one measurement value group among a plurality of measurement value groups into which the measurement values of the plurality of sensors are divided and which each comprise measurement values of a plurality of mutually adjacent sensors. The plurality of measurement value groups are subjected to the determination as to whether any of these groups contains a boundary-determining change in characteristic value, and only those measurement value groups which are determined to contain no boundary-determining change are subjected to the updating of correction values for correcting the measurement values belonging to these groups.

Also, in this embodiment, the number of the sensors which have their measurement values corrected with the correction values is limited in such a manner that the ratio of the number of these sensors to the total of the sensors is below a predetermined value.

DESCRIPTION OF THE PREFERRED EMBODIMENTS

The present invention will now be described with reference to the accompanying drawings.

First, descriptions will be given concerning several conditions which the determination according to the Present invention should satisfy.

The following descriptions concern the case where determination is made by measuring the reflectivity of light.

a) The apparent distribution ratio between a fluid in the tank, such as water or another liquid, and particles in the tank, such as anions and cations, incessantly changes, thereby causing apparent changes in the reflectivity of the light projected onto the particles. The determination should not be influenced by such apparent changes in reflectivity.

b) Some of the particles adhere to the inner surface of a transparent window of the tank. Therefore, to determine on the basis of measurements covering a small area involves the risk of errors in the determination. For this reason, it is necessary that the determination be made on the basis of average values that cover the whole of an adequately large area.

c) It is necessary that particles such as anions and cations be distinguished even when clad, etc. is adsorbed on the inner surface of the tank or the surface of particles, thereby causing discoloration.

d) Even when only one type of particle exists in the region which can be scanned through the window of the tank, the type of these particular particles must be known because, without determining the type of these particles, it is impossible to control ion exchange operations such as backwashing of ion exchange resins. For this reason, it is necessary that the determination be made not as a relative determination of two types but as absolute determinations of the individual types of particles.

e) If sensors are disposed on the inside of the window of the tank accommodating the particles, there is a risk that turbulence may occur, disturbing the boundaries between the fluid and the particles. For this reason, it is necessary that the sensors be disposed outside the window.

The window of the tank comprises a member made of glass or an acrylic resin and fitted on an opening of the tank. In general, the window member is thick enough to be flush with the inner surface of the tank, so as to avoid turbulence.

This means that particles in the tank must be distinguished on the basis of the result of scanning performed through a thick window member, hence, the scanning must be positive enough to serve this purpose.

Next, the principles of the presnet invention will be described concerning an ion exchange resin distinguishing method by way of example.

Figure 5:
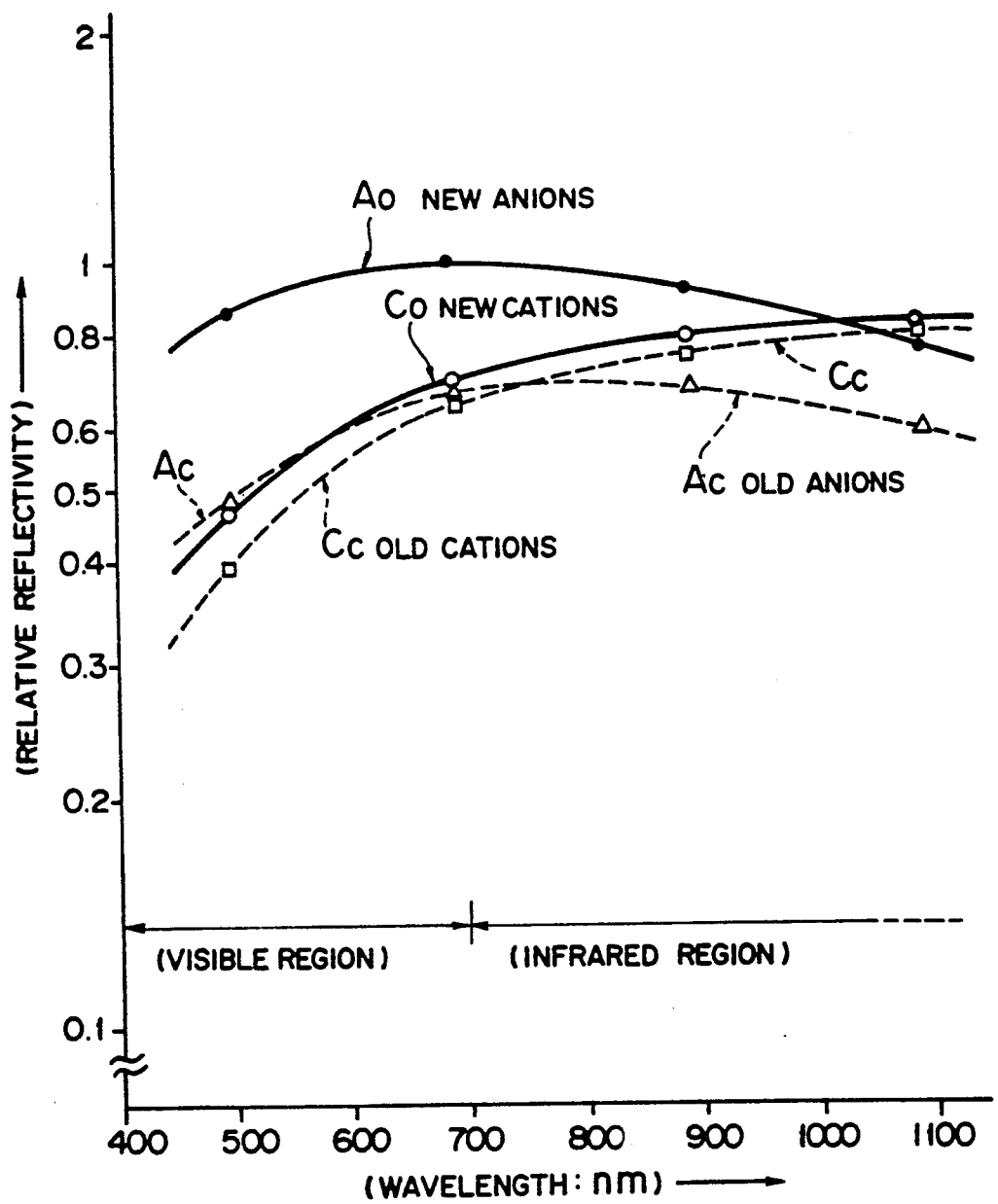
FIGS. 5 is a graph showing curves representing the characteristics of subjects of measurement with respect to the reflectivity of light, the subjects being accommodated in the tank.

FIG. 5 shows curves representing the relative reflectivities of the light at various wavelengths reflected by anions 11 and cations 12 in water 13 (see FIG. 1), and shows the characteristics with respect to the reflectivities (hereinafter referred to as "reflective characteristics") of particles with clad adsorbed thereon, i.e., old particles, and particles with no clad, i.e., new particles. In FIG. 5, the reflectivity of light having a wavelength of 700 nm and being projected onto anions 11 is represented as 1. Curves $A_0$ and $C_0$ in solid lines represent the relative reflective characteristics of new anions 11 and new cations 12, respectively, while curves $A_c$ and $C_c$ in broken lines represent the relative reflective characteristics of old anions 11 and old cations 12.

As represented by the curves $A_0$ and $A_c$, the reflectivities of light reflected by new and old anions 11 peak in the vicinity of a wavelength range of from 700 to 800 nm, and are lower at wavelengths falling outside this range. On the other hand, as represented by the curves $C_0$ and $C_c$, the reflectivities of light reflected by new and old cations 12 increase with increases in the wavelength of the light projected. Utilizing this difference in reflective characteristic, therefore, if two or more beams having different wavelength bands are projected onto particles, and the ratio between the reflectivities of the beams is calculated, it is possible to individually identify some of particles the as anions 11, and others as cations 12.

All of the characteristic curves $A_0$, $A_c$, $C_0$ and $C_c$ undergo a parallel shift to upper positions, as viewed in FIG. 5, when the distribution ratio between the particles and the water changes. For this reason, although it is possible to individually identify anions 11 and cations 12 by utilizing the above-described difference in reflective characteristic, their distinguishing is not easy with the use of a single beam. On the other hand, when what is accommodated in the tank consists substantially entirely of water, all of the characteristic curves $A_0$, $A_c$, $C_0$ and $C_c$ undergo a parallel shift to lower positions, as viewed in FIG. 5, representing very small reflectivities.

Figure 6A:
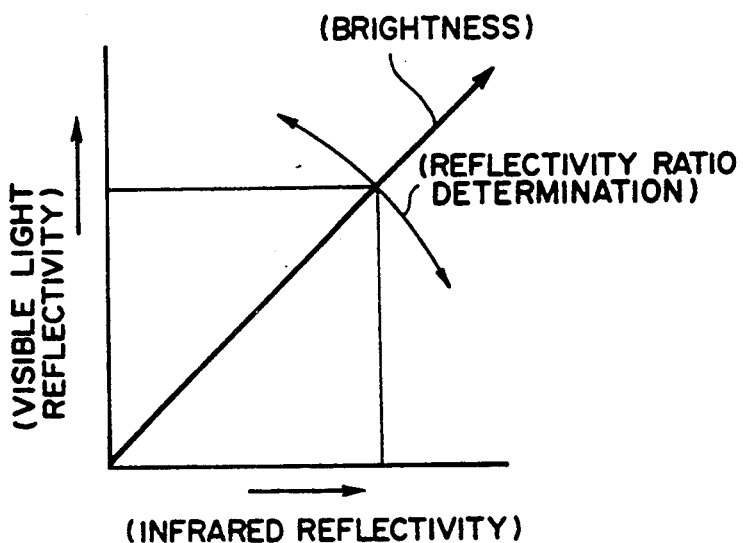
FIGS. 6 (a) and 6 (b) are graphs used to explain the principles of distinguishing performed in the embodiment.
Figure 6B:
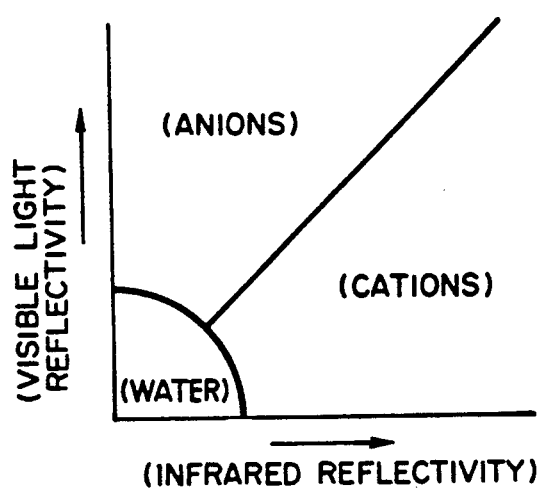
Figure 8:
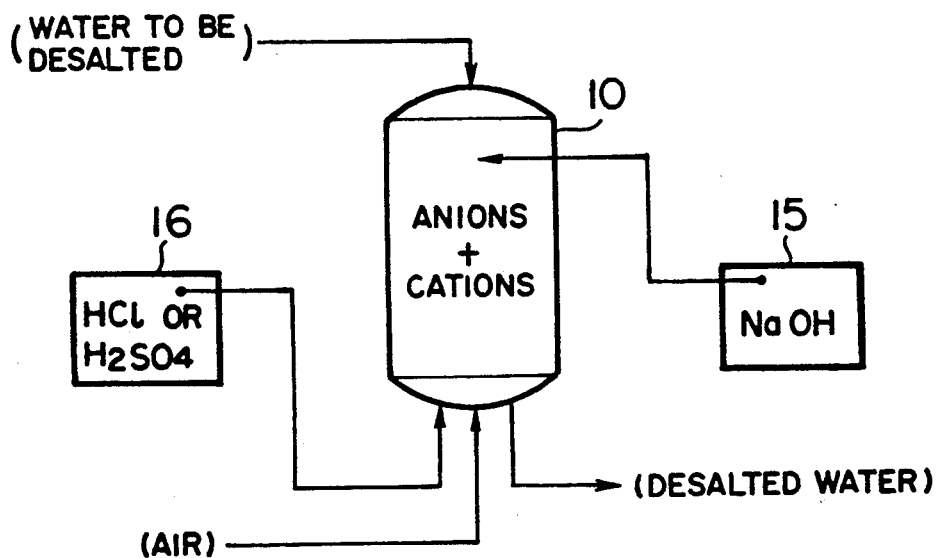
FIG. 8 is a view used to explain an example of a generally known mixed-bed deionizer.

The above-described ratios between the beams reflected by anions 11 and cations 12 are used in the following manner to identify the particles. For instance, an infrared beam and a visible beam are employed as beams having two different wavelength bands, and a composite vector of the reflectivities of the two beams is obtained using, as shown in FIGS. 6 (a) and 6 (b), the abscissa representing the reflectivity of the infrared beam and the ordinate representing the reflectivity of the visible beam. As shown in FIG. 6 (a), the composite vector is such that: as the distance of the end point of the vector from the origin increases, the brightness increases; and as the slope of the vector decreases, the reflectivity of the infrared beam increases relatively, whereas, as that slope increases, the reflectivity of the visible beam increases relatively. When the area defined by the axes is conceptionally divided into sub-areas which each solely correspond to anions 11, cations 12 or water 13, the areas will be as those shown in FIG. 6 (b).

The anions 11 and cations 12 are individually identified in the following manner. In FIG. 6 (b), the area corresponding to the water 13 is omitted, and the ratio of the reflectivity of the visible beam to that of the infrared beam is compared with a certain value serving as a distinction boundary setting value B. That is, if the measurement value RK of the reflectivity of the visible beam and the measurement value RI of the reflectivity of the infrared beam satisfy the relation (RK/RI)>B, the scanned particles are identified as anions 11, whereas if these measurement values RK and RI satisfy the relation (RK/RI)>B, the scanned particles are identified as cations 12.

It is known from certain experiments that the selection of two or more beams having a wavelength in the visible region of, for instance, from 500 to 700 nm, and a wavelength in the infrared region of, for instance, from 800 to 1100 nm, makes it possible to correctly distinguish resins regardless of whether they have never been used before or have already adsorbed clad even when there are some errors in measurement.

Figure 1:
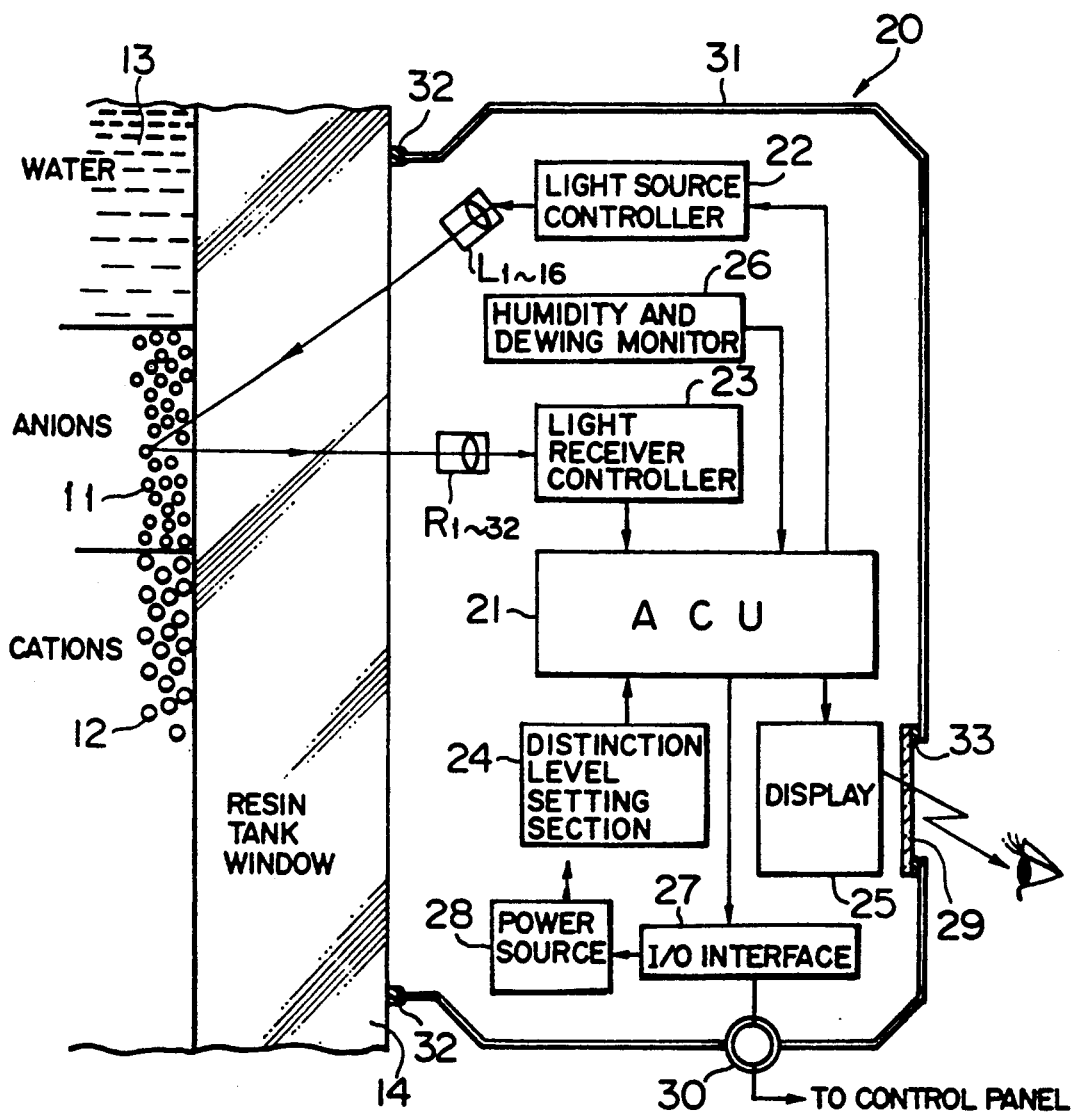
FIG. 1 is a view showing the system and construction of an apparatus according to one embodiment of the present invention.

An apparatus according to one embodiment of the present invention will now be described. FIG. 1 shows, in a block diagram, the system and construction of the apparatus, and FIG. 2 shows, in a perspective view, an example of a combination of an ion exchange resin distinguishing apparatus 20 (the apparatus of the embodiment) with an ion exchange tank 10 on which the apparatus 20 is mounted.

Figure 2:
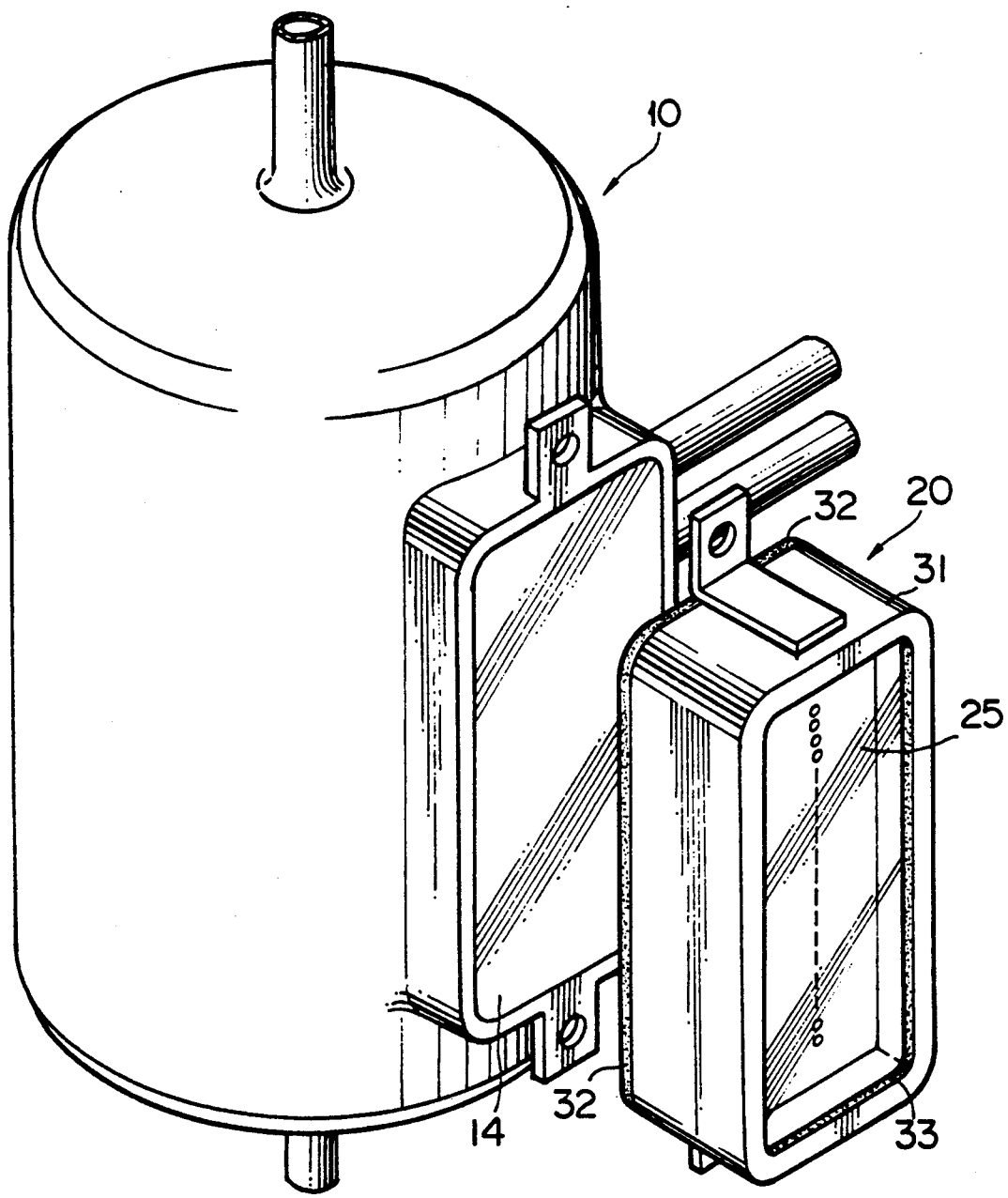
FIG. 2 is a perspective view showing the apparatus shown in FIG. 1 together with an ion exchange tank.

As shown in FIG. 2, the apparatus 20 embodying the present invention is associated with the ion exchange tank 10, and is mounted onto a window 14 provided on the front surface of the tank 10, with a rubber packing 32 interposed between the apparatus 20 and the window 14. The window 14 has a transparent and flat surface. In FIG. 2, the apparatus is shown as being disassembled from the tank 10.

The ion exchange tank 10 usually contains, on the inside thereof which is visible through the transparent window 14, anions 11 and cations 12, both contained in a liquid such as water 13.

The apparatus 20 has a housing 31 accommodating therein the following: a plurality of light emitters $L_1$, $L_2$, ... $L_{16}$ which are controlled by a light source controller 22 and which each comprise two integrated light-emitting elements capable of independently emitting two beams having different wavelengths; a plurality of light receivers $R_1$, $R_2$, ... $R_{32}$ comprising a plurality of light-receiving elements each capable of responding to light having wavelengths ranging from a visible region to an infrared region; a light receiver controller 23; an arithmetic and control unit (ACU) 21 for controlling the light source controller 22, for measuring, on the basis of the outputs of the light-receivers $R_1$ to $R_{32}$ supplied via the light receiver controller 23, the reflectivities of the beams reflected from the subject of measurement (i.e., anions 11, cations 12 or a liquid such as a water, which is scanned by the beams), and for determining what the subject of measurement is; a distinction level setting section 24 for setting reference values on the basis of which the ACU 21 makes determinations concerning the subject of measurement; and a display 25 for displaying the result of the determination of the ACU 21.

The apparatus also includes: an I/O interface 27 through which the system of the apparatus is connected to an external control panel, not shown; and a power source 28 for supplying power to various sections of the apparatus.

The display 25 is disposed in such a manner that its display surface is visible through a transparent plate 29 from the outside of the apparatus, with a rubber packing 33 being interposed between the transparent plate 29 and the housing 31. In addition, the above-mentioned rubber packing 32 is interposed between the housing 31 and the window 14 of the ion exchange tank 10 on which the apparatus 20 is mounted, and the I/O interface 27 is connected with a cable extending from the (unillustrated) control panel by a connecting plug 30 of a water-proof type. Thus, when the apparatus 20 of the embodiment is mounted on the ion exchange tank 10, they together form an dust-proof, water-proof, and air-tight assembly.

Furthermore, a drying agent, not shown, is disposed in the interior of the apparatus 20, and a humidity and dewing monitor 26 is provided to check whether there is any abnormal increase in the humidity within the apparatus or any dewing. When there is any hindrance to the measurement of reflectivity, such as fogging of the surface of the transparent window 14, the ACU 21 operates, on the basis of the output of the humidity and dewing monitor 26, to generate an alarm to the control panel.

Figure 3:
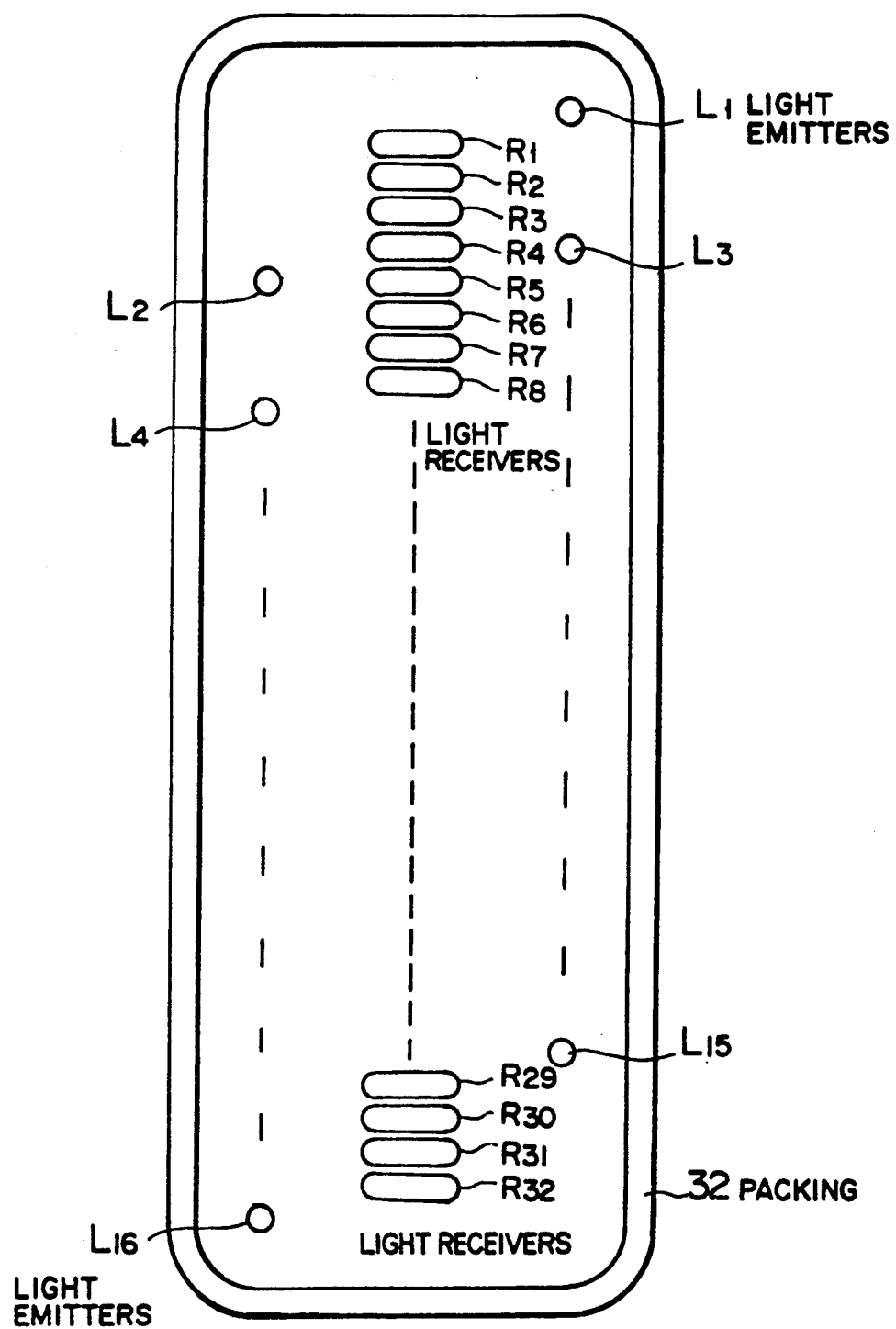
FIG. 3 is a rear view of the apparatus shown in FIGS. 1 and 2, seen from the side close to the ion exchange tank.

FIG. 3 is a view of the rear of the apparatus 20 taken from the side of the tank 10 showing an example of the arrangement of the light emitters $L_1$, $L_2$, ... $L_{16}$ and the light-receivers $R_1$, $R_2$, ... $R_{32}$.

The light-receivers $R_1$, $R_2$, ... $R_{32}$ are arranged on the apparatus 20 in a row extending in the vertical direction with respect to the tank. The light-receivers $R_1$ to $R_{32}$ comprise a plurality of built-in light-receiving elements in front of which are disposed suitable slits or the like so that these elements are capable of responding only to light normally incident thereon and of generating outputs indicative of the received light.

The light emitters $L_1$, $L_2$, ... $L_{16}$ are such that the light emitters $L_1$ and $L_2$ form a first pair which emit beams in correspondence with a first set of the light-receivers $R_1$, $R_2$, $R_3$ and $R_4$, and the light emitters $L_3$ and $L_4$ form a second pair which emit beams in correspondence with a second set of the light-receivers $R_5$, $R_6$, $R_7$ and $R_8$. The remaining light emitters $L_5$, $L_6$, ... $L_{16}$ form like pairs which correspond to like sets of the light-receivers $R_9$, $R_{10}$, ... $R_{32}$.

The paired light emitters, e.g., $L_1$ and $L_2$, are disposed in such a manner that the light emitted by these elements in the main radiation direction is obliquely incident upon the transparent window 14 confronting the corresponding light-receivers, e.g., $R_1$ to $R_4$. This is for the purpose of avoiding any entrance of the light reflected from the transparent window 14 into the light-receivers, hence, avoiding any error in the measurement of the quantity of light reflected from the subject of measurement.

Further, the paired light emitters, e.g., $L_1$ and $L_2$, are disposed on either side of the corresponding set of light-receivers, e.g., $R_1$ to $R_4$. This is for the purpose of preventing resin particles serving as the subject of measurement from becoming shaded, hence, preventing any error in the measurement of the reflectivities.

The light emitters $L_1$, $L_2$, ... $L_{16}$ emit light in such a manner that each pair of light emitters, e.g., $L_1$ and $L_2$, alternately emit a beam whose wavelength is in the infrared region and a beam whose wavelength is in the visible region, each beam being emitted for a very short period of time, so as to irradiate a part of the subject of measurement which is in front of the corresponding light-receivers, e.g., $R_1$ to $R_4$. The light-receiving elements of the light-receivers receive the light reflected from the irradiated part of the subject, and generate outputs corresponding to the received light, which are then input to the light receiver controller 23.

Upon receiving the inputs, the light receiver controller 23 performs a logarithm compression of the outputs of the light-receivers, e.g., $R_1$ to $R_4$, whose periods are in synchronization with the driving of the corresponding light emitters, e.g., $L_1$ and $L_2$, and sends the compressed data as digital signals to the ACU 21.

The ACU 21 makes determinations concerning anions, cations and water (or other liquid) with reference to the levels set by the distinction level setting section 24. The results of the determinations are displayed by the display 25, and are also output to the external control panel via the I/O interface 27 and the water-proof connecting plug 30. The control panel performs, on the basis of the sent results, automatic operations such as valve adjustments necessary to an ion exchange operation.

Figure 4:
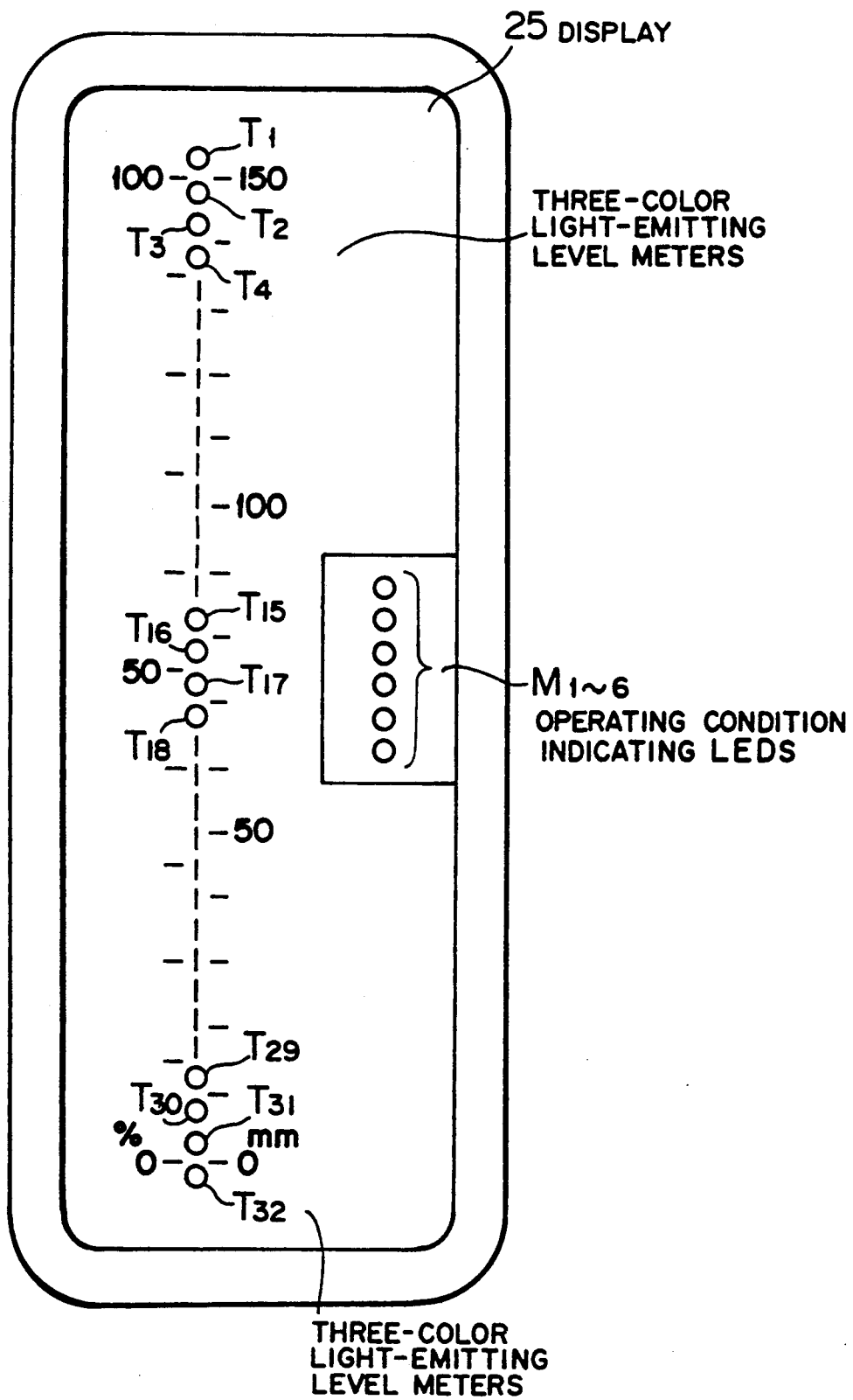
FIG. 4 is a front view of the apparatus of FIGS. 1 and 2, seen from the remote front of the apparatus.

FIG. 4 is a view taken from the front of the apparatus 20 which is remote from the tank 10, showing the display surface of the display 25 which is visible through the transparent plate 29 of the apparatus, and illustrating an example of the arrangement of a plurality of three-color light-emitting level meters $T_1, T_2 \ldots T_{32}$ (hereinafter abbreviated to "level meters") and operating condition indicating light-emitting diodes (LEDs) $M_1, M_2 \ldots M_8$. The level meters are such that the level meter $T_1$ corresponds to the light receiver $R_1$ (in FIG. 3), the level meter $T_2$ corresponds to the light receiver $R_2$, and the remaining level meters are in like correspondence, with the level meter $T_{32}$ corresponding to the light receiver $R_{32}$. Each of the level meters $T_1$ to $T_{32}$ indicates the result of the determination on the basis of the output from the corresponding light receiver by, for instance, emitting light in green to indicate the existence of water, emitting light in yellow to indicate the existence of anions, and emitting light in red to indicate the existence of cations.

The operating condition indicating LEDs $M_1, M_2 \ldots M_8$ provide from-moment-to-moment indications of various conditions of the operation currently performed, concerning, for instance, whether or not the apparatus interior drying agent is normal, whether or not the apparatus interior humidity is normal, and whether or not anions alone are detected.

Figure 7A:
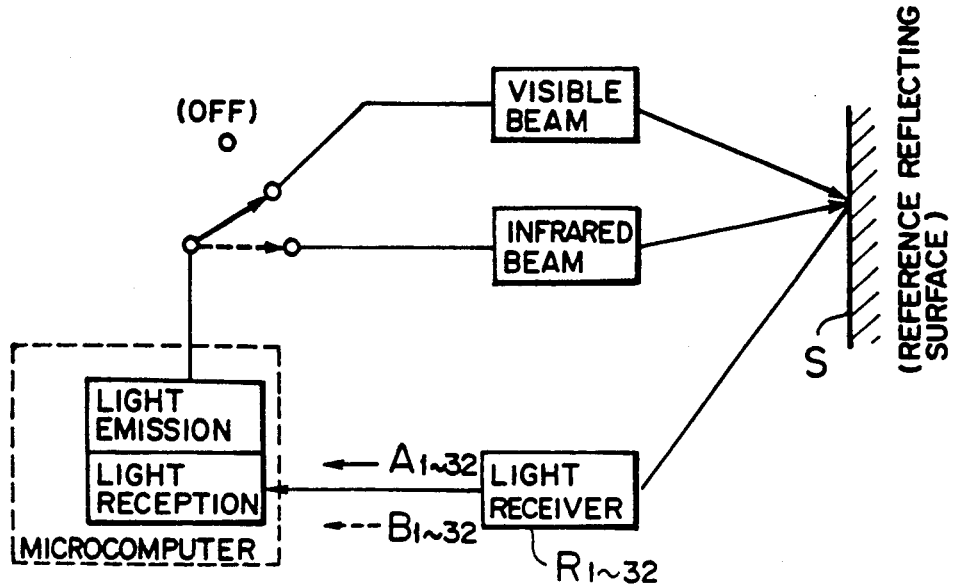
FIGS. 7 (a) to 7 (c) are views used to explain an example of a calibration method applied to a reflectivity measuring means of the embodiment.
Figure 7B:
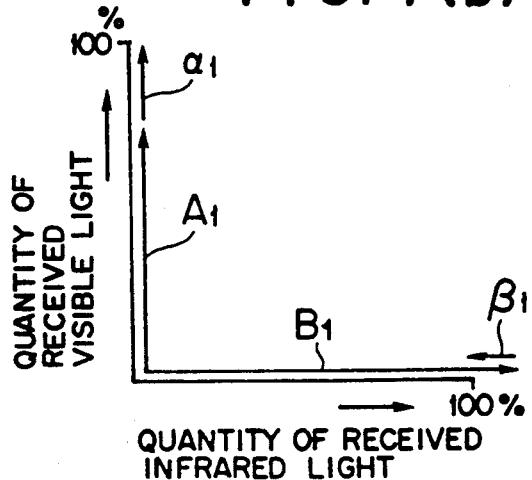
Figure 7C:
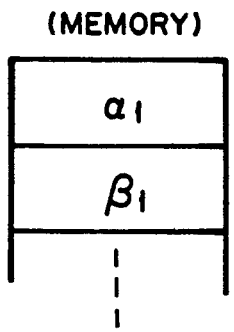
Figure 9D:
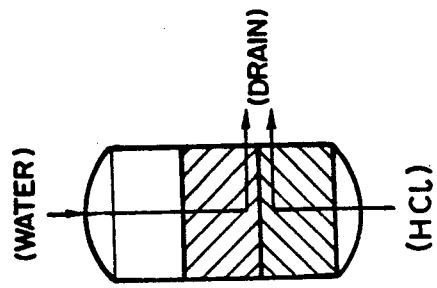
FIGS. 9 (a) through 9 (g) are views used to explain an example of the operation of the mixed-bed deionizer of FIG. 8.
Figure 9C:
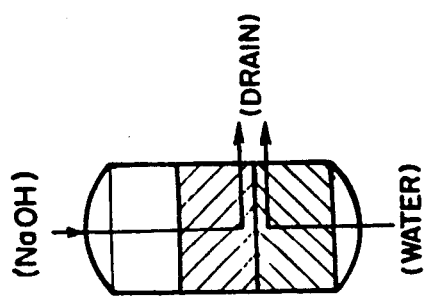
Figure 9B:
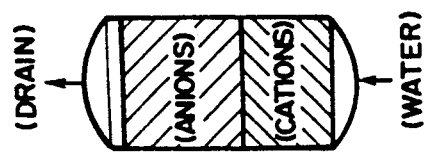
Figure 9A:
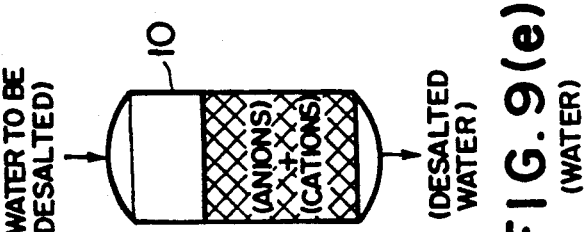
Figure 9G:
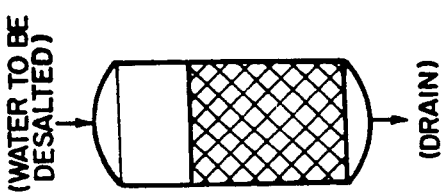
Figure 9F:
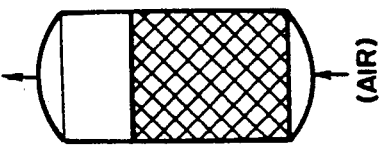
Figure 9E:
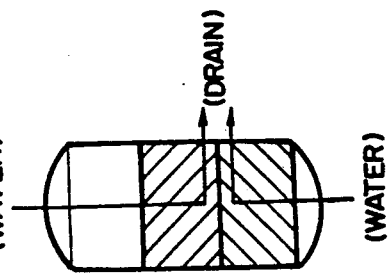

Referring to FIGS. 7 (a) to 7 (c), there is shown an example of a means for performing automatic calibration which the apparatus 20 of the embodiment includes to distinguish ion exchange resins.

The calibration is performed either before the apparatus 20 is mounted on the associated ion exchange tank 10 or after the apparatus 20 is dismounted therefrom for the purpose of maintenance checking. In this embodiment, separately from the calibration, suitable correction of the characteristics of the individual sensors is performed, as will be described later, at timings arbitrarily set, for instance, at an interval between two successive measurements during the operation of the apparatus.

FIGS. 7 (b) and 7 (c) illustrate a method which is mainly used to correct variations in the characteristics of the elements constituting the light emitters $L_1, L_2, \ldots L_{16}$ and light-receivers $R_1, R_2, \ldots R_{32}$, as well as their changes in characteristics with the passage of time.

The calibration is performed by the system shown in FIG. 7 (a) by using a reference reflecting surface S comprising, for instance, a sheet of glass for use as a window member of an industrial-use-resin tank which is disposed in front of a sheet of high-quality paper. The program in a microcomputer of the ACU 21 is switched to the calibration mode by depressing an externally operable calibration button, not shown, whereupon automatic correction of the sensitivity and the color reference values of each of the light-receiving elements (color sensors) constituting the light-receivers $R_1$ to $R_{32}$ is entered.

The correction method is such that an output $A_1$ of the light receiver $R_1$ obtained when a switch of the system shown in FIG. 7 (a) is connected for the projection of visible light, as well as an output $B_1$ of the light receiver $R_1$ obtained when the switch is connected for the projection of infrared light are plotted, as shown in FIG. 7 (b), against axes representing the 100% quantities of the received visible and infrared light. When both the ordinate axis and the abscissa axis represent quantities of light on a logarithmic scale, a value $\alpha_1$, such as that shown in FIG. 7 (b), represents the ratio in accordance with which the output of the light receiver $R_1$ caused by the projection of visible light should be corrected. Similarly, the value $\beta_1$ shown in FIG. 7 (b) represents the ratio in accordance with which the output of the light receiver $R_1$ caused by the projection of infrared light should be corrected. Likewise, ratios in accordance with which the respective outputs of the other color sensors $R_2$ to $R_{32}$ should be corrected are obtained. The obtained ratios are stored in a memory, as shown in FIG. 7 (c). The contents of the memory are used as correction values when the apparatus 20 is actually mounted on the ion exchange tank 10 for operation.

Although in the foregoing descriptions, two beams having different wavelengths are used to measure the reflective characteristic of the subject of measurement, it will be understood referring to the characteristic curves shown in FIG. 5 that the number of beams used to measure the reflectivities may be any so far as it is no smaller than two. In addition, in certain conditions of the application of the present invention, the combination of a visible beam and an infrared beam is not always necessary, and alternatively usable is a combination of a visible beam and an infrared beam including visible rays, or a combination of two types of rays in an infrared beam.

Also in the foregoing embodiments, the method of distinguishing ion exchange resins and the apparatus for the same are mere examples, and the embodiments may be generally used to determine the individual existence of a first group of particles contained in a liquid and a second group of particles in the same liquid but with characteristics different from those of the first particles.

Next, a method of processing data which is performed by the ACU 21 shown in FIG. 1 will be described.

In the data processing, it is necessary to meet the above-described requirements of the determination of boundaries between particles in flowing water, that is, to overcome such problems as apparent changes in the reflectivities of the light projected onto the particles, errors in the determination owing to a measurement covering only a small area which is in turn caused by particles adhering to the inner surface of the transparent window for scanning, and partial discoloring due to clad adsorption on the inner surface of the tank or on the surface of particles.

In view of these problems, the present invention adopts the following data processing method.

Figure 10:
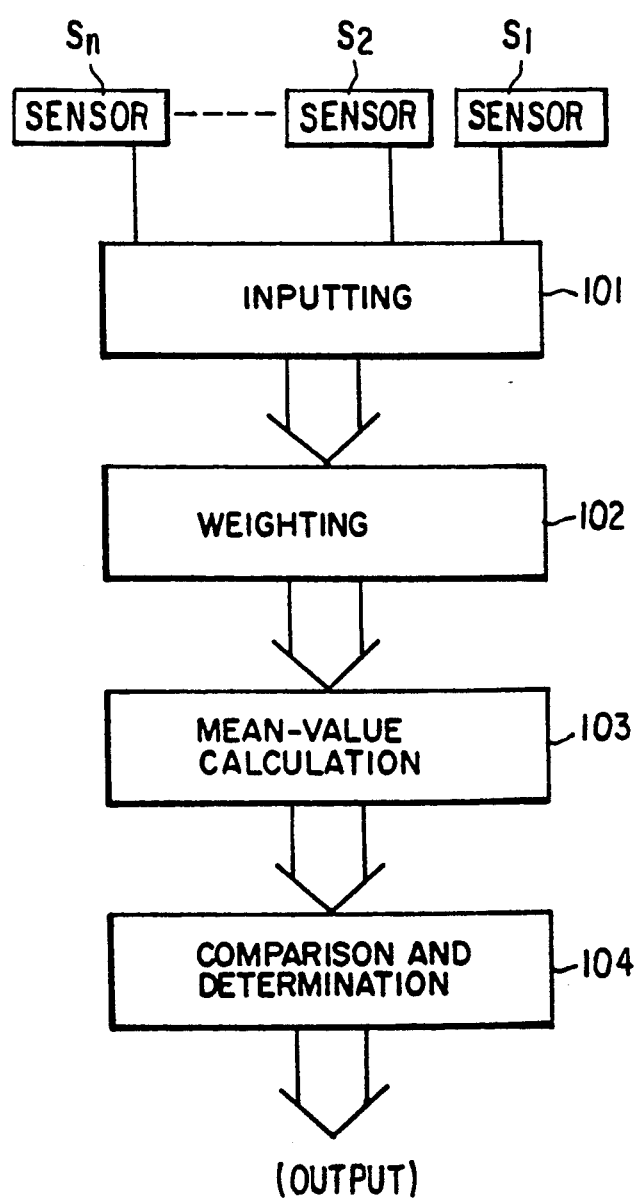
FIG. 10 is a view showing an example of the flow of procedures for processing data in the embodiment.

FIG. 10 shows an example of the flow of procedures for processing data. It is assumed that detectors $S_1$, $S_2$, ... $S_n$ (hereinafter referred to as "sensors") shown in FIG. 10 correspond to the light-receivers $R_1$ to $R_{32}$ shown in FIG. 1.

In Procedure 101 (inputting), the respective outputs of the sensors $S_1$, $S_2$, ... $S_n$ are input. The thus input measurement values from the sensors are processed by Procedure 102 (weighting), Procedure 103 (mean value calculation), and Procedure 104 (comparison and determination). The resultant output is displayed as the results of boundary determination. The above-described procedures 101 to 104 are performed in the ACU 21.

In Procedure 102, outputs $a_1$, $a_2$, $a_3$, ... $a_x$ of sensors $S_1$, $S_2$, $S_3$, ... $S_x$ are subjected to weighting before they are averaged by the mean value calculation in the subsequent procedure 103. For instance, $a_1$ is multiplied by 1, $a_2$ is multiplied by 2, and $a_3$ is multiplied by 1 in Procedure 102. If the mean value calculated in Procedure 103 is $b_2$, it is expressed as follows: $b_2=(a_1+2a_2+a_3)/4$. Thus, the weight of $a_1$ on the output of Procedure 103 is $\frac{1}{4}$, the weight of $a_2$ is $\frac{1}{2}$, and the weight of $a_3$ is $\frac{1}{4}$. Therefore, even when $a_1$, $a_2$ or $a_3$ has an anomalously great or small value which can lead to an erroneous determination, the weight of such a measurement value on $b_2$ is only $\frac{1}{4}$ or $\frac{1}{2}$.

Similarly, subsequent weighting and mean value calculation procedures are performed wherein $a_2$ is multiplied by 1, $a_3$ is multiplied by 2, and $a_4$ is multiplied by 1, and the sum of these products is averaged to obtain a mean value $b_3$. Such procedures are performed a plurality of times more whereby further mean values $b_4$, ... $b_{n-1}$ are obtained. The mean values $b_2$, $b_3$, ... $b_{n-1}$ thus obtained are used in place of the output values $a_2$, $a_3$, ... $a_{n-1}$ to determine whether or not the series $a_2$, $a_3$, ... $a_{n-1}$ involves any differences in output on the basis of which a boundary may be determined to exist.

The determination of the existence of boundaries will now be described.

As described before with reference to FIG. 5, the curves $A_0$ and $A_c$, which show the relative reflective characteristics of new and old anions 11, each peak in the vicinity of the wavelength range of from 700 to 800 nm of the light projected thereon, and are each lower in greater or smaller-wavelength ranges. On the other hand, the reflective characteristics of new and old cations 12 are such that, as represented by the curves $C_0$ and $C_c$, the relative reflectivity increases with increases in the wavelength of the light projected thereon. Therefore, when two or more beams having different wavelength bands are projected onto the subject of measurement, and the ratio between the relative reflectivities of the projected beams is calculated, it is possible to individually determine whether the scanned particles are anions 11 or cations 12.

If the subject of measurement consists substantially solely of water 13, all of the curves $A_0$, $A_c$, $C_0$ and $C_c$ shift to indicate very small relative reflectivities. Conceptionally, therefore, the areas corresponding to anions 11, cations 12 and water 13 can be set as shown in FIG. 6 (b) in relation to a certain vector.

Figure 14A:
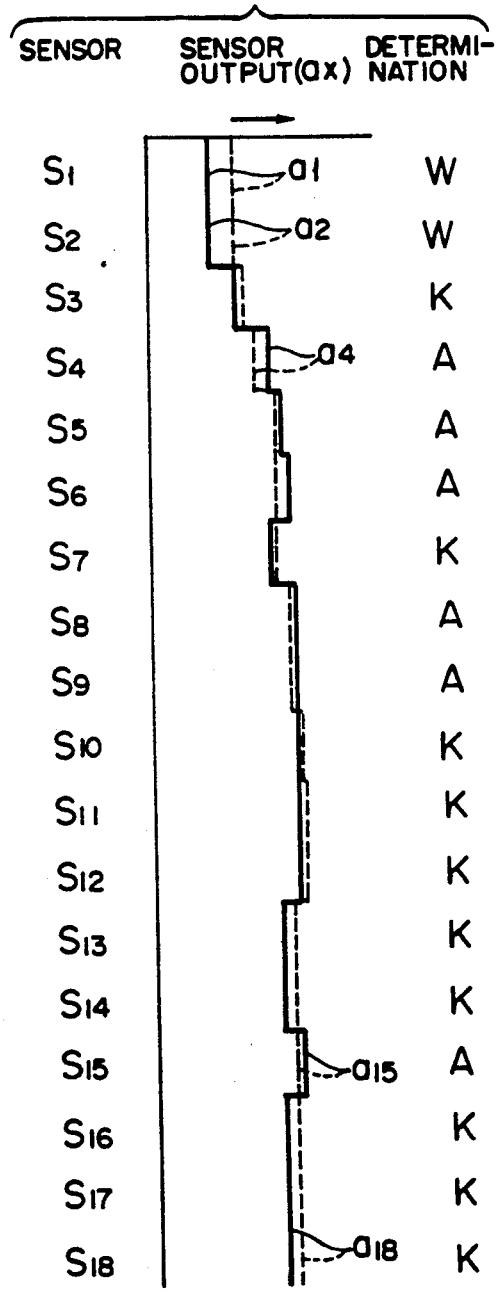
FIGS. 14 (a) and 14 (b) are views used to explain how to determine, by the procedures shown in FIG. 10, the position of boundaries in correspondence with changes in characteristic values.
Figure 14B:
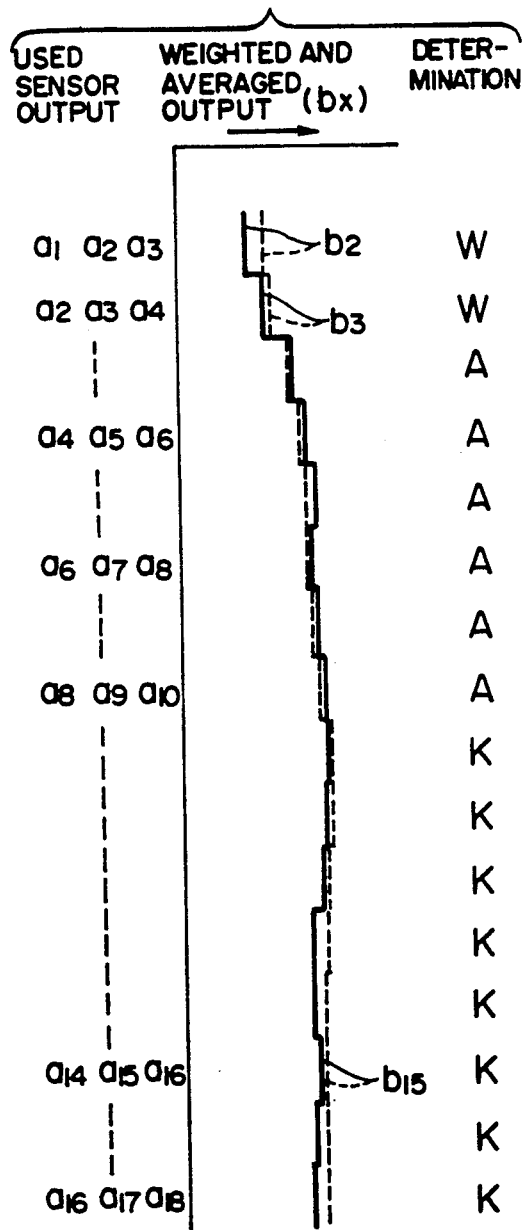

FIGS. 14 (a) and 14 (b) illustrate how the positions of boundaries are determined, the determination in FIG. 14 (b) employing the procedures shown in FIG. 10. In the illustrated example, mean values $b_2$, ... $b_{17}$ are calculated from sensor outputs $a_1$, ... $a_{18}$.

In these figures, the solid lines represent sensor outputs indicative of the reflected visible beam, and the broken lines represent outputs indicative of the reflected infrared beam. The symbols W, A and K (in the column headed by "DETERMINATION") respectively represent water, anions and cations.

In the determination shown in FIG. 14 (a), the individual existence of water, anions and cations is determined on the basis of the outputs of sensors $S_1$, $S_2$, ... $S_{18}$ which have received the two different beams (e.g., a beam in the visible region and a beam in the infrared region) reflected.

Specifically, on the basis of the outputs of the sensors $S_1$ and $S_2$ which indicate small reflectivities of both the visible beam and the infrared beam, the subject of measurement which has reflected the beams received by these sensors is determined to be water 13 (W). (Actually, an output from a sensor, represented by symbol $a_x$, comprises a pair of outputs each corresponding to the visible beam or the infrared beam.)

Similarly, on the basis of those sensor output pairs each comprising two outputs $a_x$ indicative of a greater reflectivity of the visible beam than that of the infrared beam, the subject of measurement is determined to be anions 11 (A).

Further, on the basis of those sensor output pairs each comprising two outputs $a_x$ indicative of a greater reflectivity of the infrared beam than that of the visible beam, the subject of measurement is determined to be cations 12 (K).

In the example shown in FIG. 14 (a), the outputs of the sensors $S_3$ and $S_7$ should be regarded as resulting in the determination of the existence of cations K due to influence by, e.g., a relatively large amount of cations adhering to that inner surface portion of the window 14 of the tank 10 facing these sensors because, in fact, a greater part of the region corresponding these sensors is occupied by anions.

Also, the output of the sensor $S_{15}$ should be regarded as resulting in the determination of the existence of anions A due to influence by, e.g., anions adhering to that inner surface portion of the window facing the sensor because, in fact, the region corresponding the sensor is occupied by cations.

In the determination shown in FIG. 14 (b), sensor outputs $a_x$, such as those in FIG. 14 (a), are processed by: weighting three outputs of three adjacent sensors by multiplying the output in the middle of the series of the three outputs by 2 and multiplying each of the outputs on either side of the middle output by 1; averaging the weighted outputs; and repeating such weighting and averaging until a plurality of weighted mean values are obtained. Then, the obtained weighted mean values are used in place of the sensor outputs $a_x$.

The determination shown in FIG. 14 (b) which is performed in this manner is such that the outputs of the sensors $S_3$ and $S_7$, which are regarded as indicating the existence of cations K with the determination shown in FIG. 14 (a), result in the determination of the existence of water W and anions A, and the output of the sensor $S_{15}$, which is regarded as indicating the existence of anions A with the determination shown in FIG. 14 (a), results in the determination of the existence of cations K, thereby providing results which are faithful to the actual conditions of the particles in the tank.

In the data processing shown in FIGS. 14 (a) and 14 (b), the data are processed in an analog manner before the data are compared for distinguishing.

In FIG. 14 (b), the symbol $b_x$ represents mean values each obtained by weighting three adjacent output data $a_x$ by multiplying the three outputs by 1, 2 and 1, and averaging the weighted outputs. These mean values are the same as those obtained by averaging two adjacent output values in such a manner as to obtain a plurality of mean values, and further averaging two adjacent ones of the plurality of mean values.

That is, if, for instance, $a_1$, $a_2$ and $a_3$ are outputs of three adjacent sensors $S_1$, $S_2$ and $S_3$, since the simple mean of $a_1$ and $a_2$ is $(a_1+a_2)/2$ and the simple mean of $a_2$ and $a_3$ is $(a_2+a_3)/2$, the mean value of these simple means is $(a_1+2a_2+a_3)/4$. This result coincides with the result obtained by weighting the data $a_1$, $a_2$ and $a_3$ by 1, 2 and 1, and averaging the weighted data.

Next, let us consider the case where a mean of three adjacent outputs is calculated, and such averaging is repeated until three adjacent mean values are obtained. Here, the result $C_3$ obtained from data $a_1$, $a_2$, $a_3$, $a_4$ and $a_5$ is expressed as: $C_3=(a_1+2a_2+3a_3+2a_4+a_5)/9$. When $C_3$ is used in place of the output value $a_3$, even when the output of the sensor $S_3$ is anomalously greater or smaller than the adjacent outputs, its weight on the result is $\frac{1}{3}$. Therefore, with such data processing, values which are anomalously greater or smaller than the adjacent values can be smoothed, thereby making it possible to more effectively avoid an erroneous determination.

The result of the above-described calculation is the same as that obtained by first weighting data $a_1$, $a_2$, $a_3$, $a_4$ and $a_5$ by 1, 2, 3, 2 and 1, respectively, and then averaging the weighted data.

Next, let us consider the case where the same data $a_1$, $a_2$, $a_3$, $a_4$ and $a_5$ are used and processed by calculating a plurality of first mean values each obtained by averaging two adjacent items of data, calculating a plurality of second mean values each obtained by averaging two adjacent ones of the first mean values, calculating in a similar manner a plurality of third mean values from the second mean values, further calculating in a similar manner a plurality of fourth mean values from the third mean values, and finally calculating the mean of the fourth mean values. In this case, the resultant mean $d_3$ is expressed as: $d_3=(a_1+4a_2+6a_3+4a_4+a_5)/16$. This result coincides with the result obtained by first weighting data $a_1$, $a_2$, $a_3$, $a_4$ and $a_5$ by 1, 4, 6, 4 and 1, respectively, and then averaging the weighted data.

In this way, a means provided for the weighting procedure 102 shown in FIG. 10 may be loaded with software which performs either the multiplications of the data ($a_1$, $a_2$, etc.) to be averaged by coefficients for direct weighting or the repeated calculations of mean values of adjacent values. In general, a repetition of fixed-form calculations involves simpler construction of hardware and higher speed of calculation.

Various weighting coefficients (or any equivalent forms of calculation) are possible. Suitable coefficients or the like are selected by considering the degree by which anomalous values can be greater or smaller than the adjacent values, the degree by which a value is influenced by adjacent values, and in accordance with the nature of the characteristic the sensors are required to detect.

Figure 11:
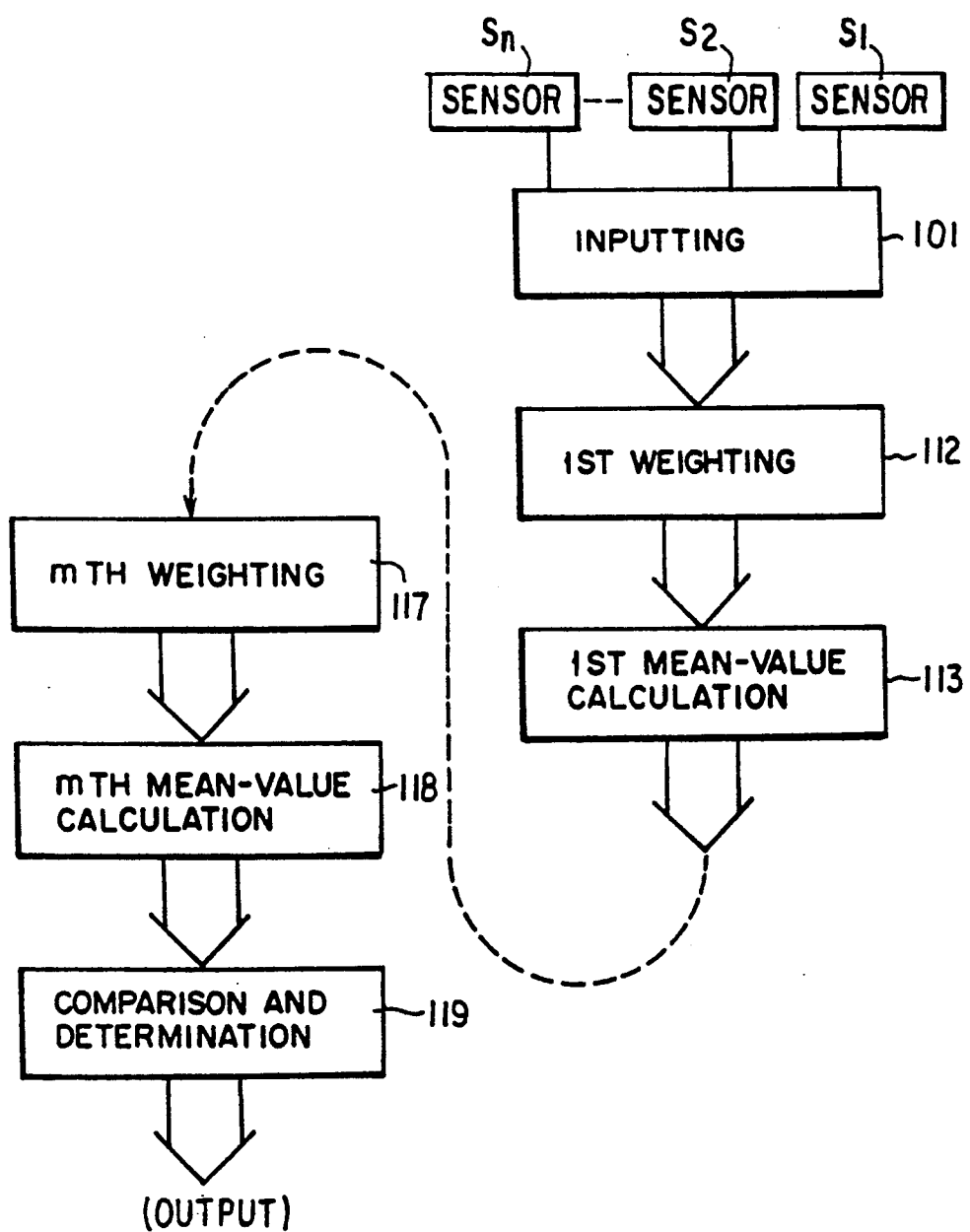
FIG. 11 is a view showing another example of the flow of procedures for processing data in the embodiment of FIG. 1.

FIG. 11 shows a modification of the data processing for comparison and determination, which may be adopted when it is desired that irregularities in the measurement values be smoothed to a greater extent.

In the processing shown in FIG. 11, Procedure 102 (weighting) and Procedure 103 (mean value calculation), both shown in FIG. 10, are substituted by Procedure 112 (first weighting) and Procedure 113 (first mean-value calculation) which are followed by like procedures until Procedure 117 (mth weighting) and Procedure 118 (mth mean-value calculation) are performed. In this processing, weighting and averaging are repeated m times, that is, they are repeatedly executed m times.

As the number of repetition increases, the result of calculation becomes less influenced by erroneous values. However, the number of the sensors added to the start and the end of a series of sensors arranged in a row inevitably increases, complicating the entire apparatus.

The data processing may be performed in the following manner to efficiently detect boundary-determining changes in the characteristic values.

Figure 12:
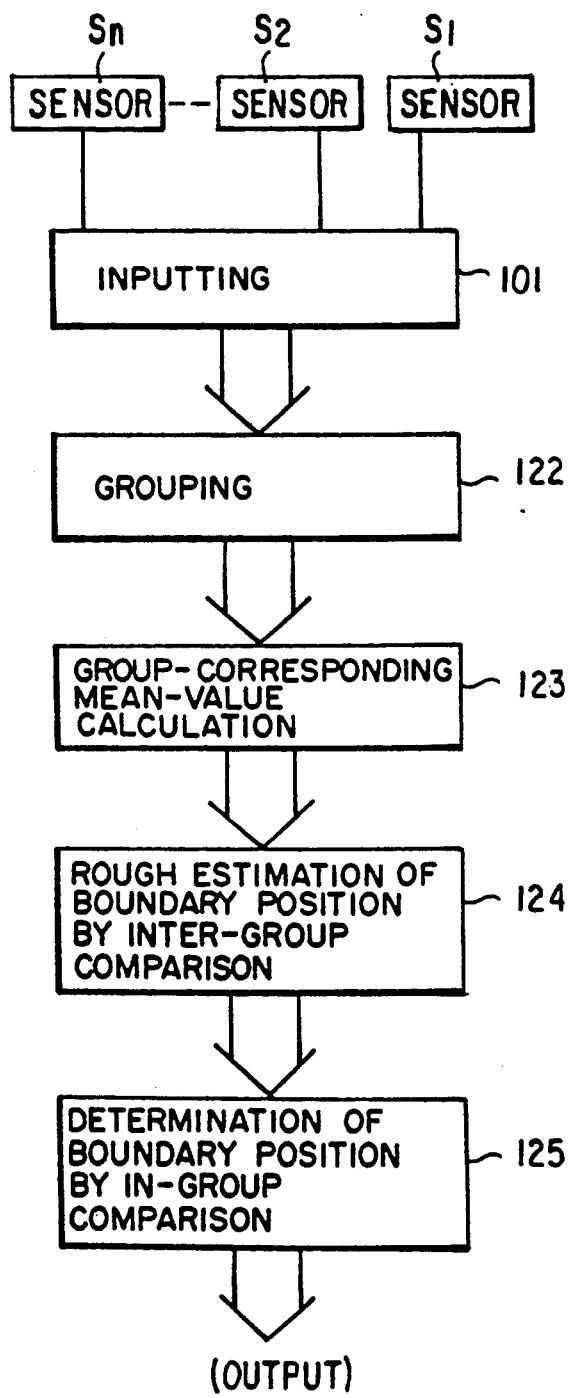
FIG. 12 is a view showing an example of the flow of procedures for processing data in the embodiment of FIG. 1, which procedures are directed to a higher efficiency.

FIG. 12 shows the flow of procedures for such data processing. Similarly to the procedures shown in FIG. 10, it is assumed that $a_1$, $a_2$, ... $a_n$ are outputs of sensors $S_1$, $S_2$, ... $S_n$. In Procedure 122, the outputs are divided into a plurality of groups each comprising, e.g., three outputs. In Procedure 123, the mean values of the individual groups are calculated, which will be denoted as $C_1$, $C_2$, ... $C_6$. Thus, the mean values $C_1$, $C_2$, ... $C_6$ calculated from the sensor outputs $a_1$ to $a_{18}$, corresponding in status to those in FIG. 14 (a), are expressed as: $C_1=(a_1+a_2+a_3)/3$, $C_2=((a_4+a_5+a_6)/3$, et seq. (the last of the series being $C_6=(a_{16}+a_{17}+a_{18})/3$). These values are illustrated in FIG. 15.

Figure 15:
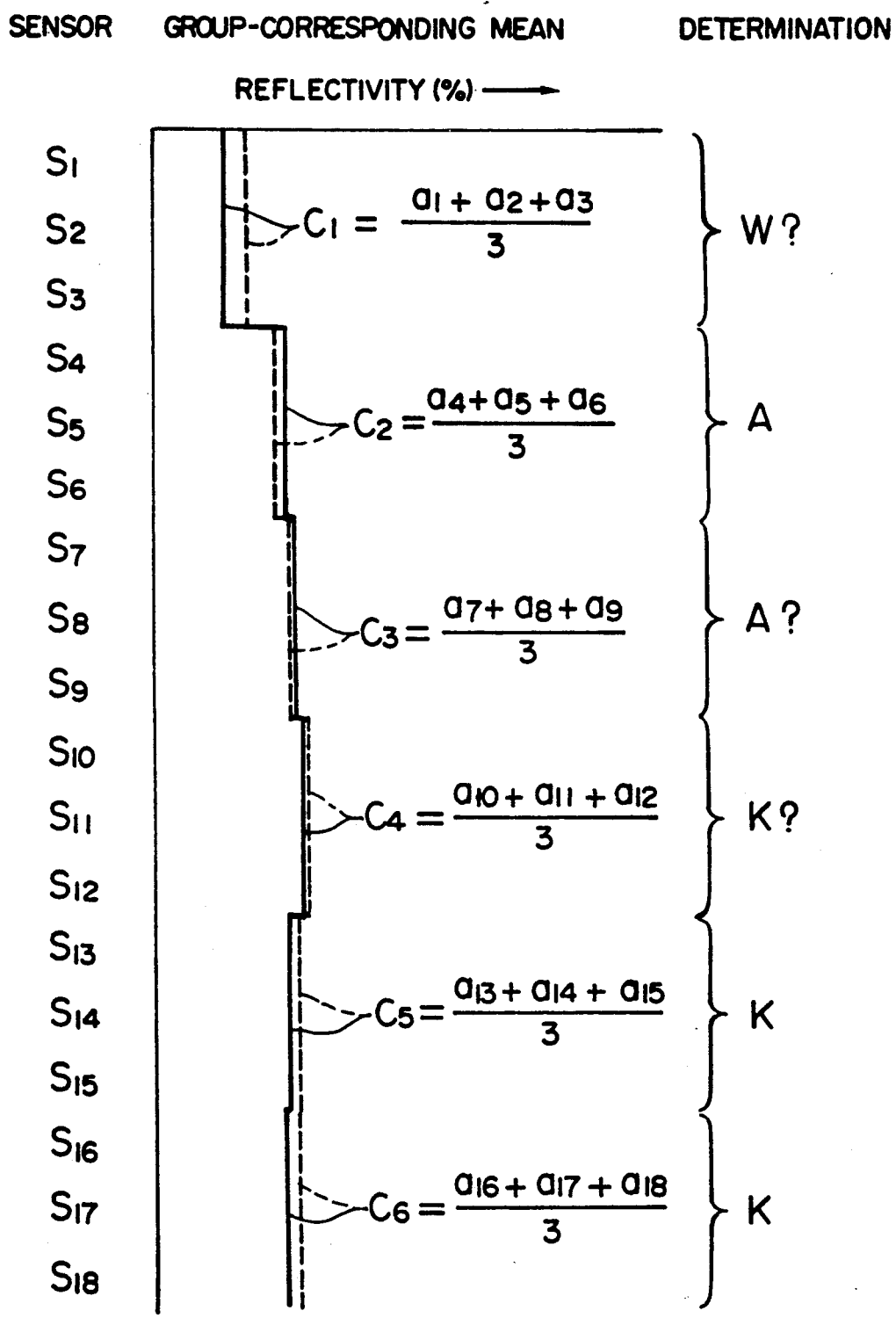
FIG. 15 is a view used to explain how to narrow, by the procedures shown in FIG. 12, ranges possibly containing boundary-determining changes.

In FIG. 15, the solid lines indicate the reflectivities of a visible beam, while the broken lines indicate the reflectivities of an infrared beam.

From the group-corresponding mean value $C_1$ which indicates both a small reflectivity of the visible beam and a small reflectivity of the infrared beam, the region concerned is regarded as being substantially entirely occupied by water W. However, since it is possible that anions are contained in this region, it is necessary to further examine the data constituting the group by using a finer grouping.

From the group-corresponding mean value $C_2$ which indicates a sufficiently greater reflectivity of the visible beam than that of the infrared beam, it is estimated that all of the data $a_4$, $a_5$ and $a_6$ constituting the corresponding group concern anions A.

The group-corresponding mean value $C_3$ indicates a greater reflectivity of the visible beam than that of the infrared beam, however, with a small difference between the reflectivities. Therefore, although the region concerned can be regarded as substantially entirely occupied by anions A, it is also possible that cations may be contained in part of this region. Therefore, it is necessary to further examine the data in the group by using a finer grouping.

The group-corresponding mean value $C_4$ indicates a greater reflectivity of the infrared beam than that of the visible beam, however, with a small difference between the reflectivities. Therefore, although the region concerned can be regarded as substantially entirely occupied by cations K, it is also possible that anions may be contained in part of this region. Further examination of the data in the group by using a finer grouping is necessary.

Each of the group-corresponding mean values $C_5$ and $C_6$ indicates a sufficiently greater reflectivity of the infrared beam than that of the visible beam. Therefore, it is estimated that all of the data in the group concern cations K.

On the basis of the above-described estimation and on the basis of the fact that water, anions and cations in a tank normally distribute vertically from above to below in the mentioned order, in Procedure 124, detailed examination of only the sensor outputs $a_1$ to $a_3$ and $a_7$ to $a_{12}$ is performed, while omitting detailed examination of the sensor outputs $a_4$ to $a_6$ and $a_{13}$ to $a_{18}$, thereby roughly determining the positions of the boundaries.

In the subsequent procedure 125, only those data that must be further examined are subjected to procedures, such as Procedures 102, 103 and 104 shown in FIG. 10, thereby obtaining results of the same type as those shown in FIG. 14 (b).

Incidentally, the determination shown in FIG. 14 (a) is such that, since the number of the sensors, hence, the number of items of the data obtained is not very great, the determination might not be very effective. However, if a greater number of items of data are input, the determination is advantageous in that it requires a reduced time.

Figure 13:
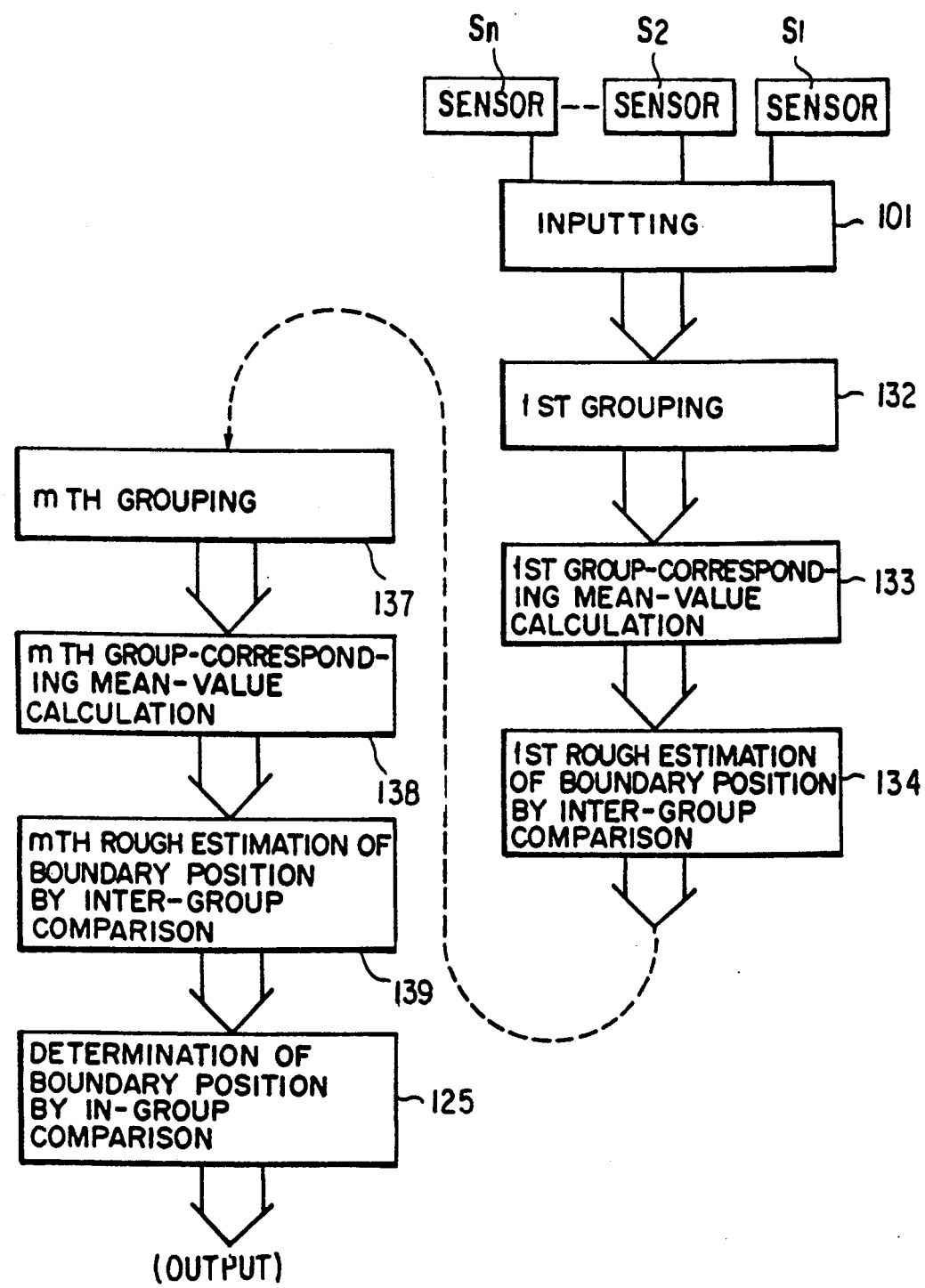
FIG. 13 is a view showing another example of the flow of procedures for processing data in the embodiment of FIG. 1, which procedures are directed to a higher efficiency.

FIG. 13 shows procedures for the data processing, which can be advantageously adopted when a great number of data are input.

The system shown in FIG. 13 differs from the system in FIG. 12 in that Procedure 122 (grouping), Procedure 123 (group-corresponding mean-value calculation), and Procedure 124 (rough estimation of boundary position by inter-group comparison) are substituted by Procedure 132 (first grouping), Procedure 133 (first group-corresponding mean-value calculation), 134 (first rough estimation of boundary position by inter-group comparison), et seq., the last three procedures of the series being Procedure 137 (mth grouping), Procedure 138 (mth group-corresponding mean-value calculation), and Procedure 139 (mth rough estimation of boundary position by inter-group comparison). Thus, in this data processing, grouping, calculation of a mean value in correspondence with each of the groups, and rough estimation of boundary position(s) on the basis of the mean values are repeated m times.

In the first to mth execution, the groupings are performed, with the number of data constituting one group differing in a multi-stage manner. Specifically, in the first grouping procedure 132, the number of the items of data belonging to each of the groups is larger than any of the corresponding numbers in the subsequent groupings, the number of the items of data in one group being the second largest in the second grouping, the number thereafter decreasing in successive stages until, in the last or mth grouping Procedure 137, the data is divided into groups each comprising the smallest number of items. The stages in which the number is decreased may be such that, when, for instance, 81 items of data are input in total, the number of one group is successively decreased to 27, 9 and 3, or when the total of the input items of data is 64, the number of one group is successively decreased to 32, 16, 8, 4 and 2.

If, as a result of the execution of Procedure 133 (first group-corresponding mean-value calculation), there are groups which possibly contain boundary-determining changes, only these groups are subjected to the second grouping (not shown in FIG. 13).

On the basis of the result of the second group-corresponding mean-value calculation, the second rough estimation of boundary position by inter-group comparison (not shown) is performed to discriminate groups which possibly contain boundary-determining changes. These groups are then subjected to the third grouping (not shown). In this way, a range which possibly contains data indicating a boundary position is narrowed to a sub-range which most possibly contain the boundary position.

Finally, in Procedure 125 (determination of boundary position by in-group comparison), the correct position of the boundary is determined.

The procedure 125 (determination of boundary position by in-group comparison) in each of FIGS. 12 and 13 may employ either of the determination manners shown in FIGS. 10 and 11.

In this embodiment, separately from the calibration described before with reference to FIGS. 7 (a) to (c), suitable correction of the characteristics of the individual sensors is performed at timings arbitrarily set, for instance, at an interval between two successive measurements during the operation of the apparatus.

The sensor output calibration shown in FIGS. 7 (a) to (c) is adapted to automatize a conventional calibration method and to correct the sensor characteristics in correspondence with beams at the two frequency bands to be used. Although this calibration method is precise, it is inefficient because of various limitations, hence, it cannot be performed at any time desired.

Figure 16A:
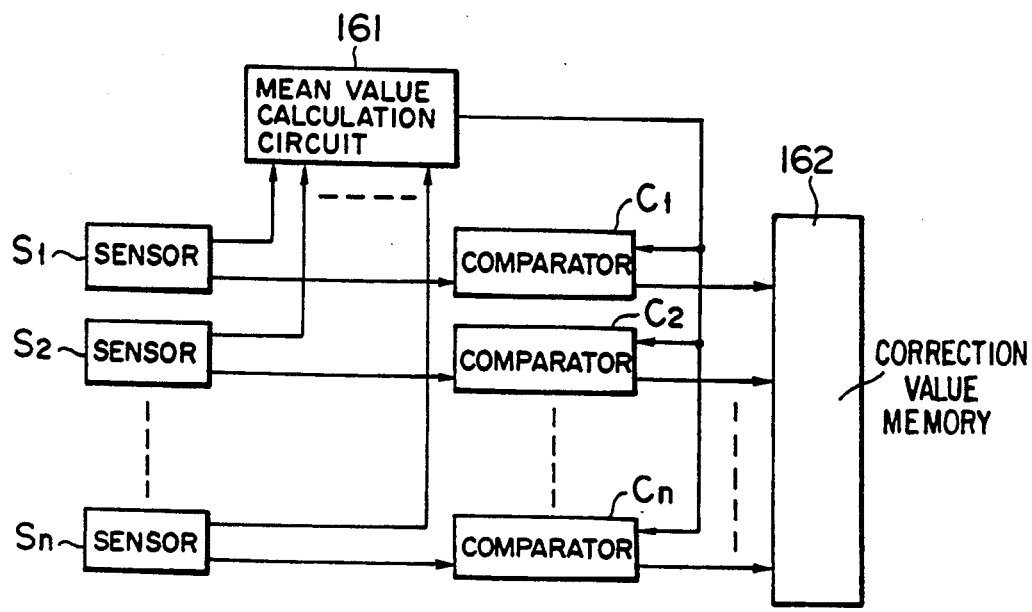
FIGS. 16 (a) and 16 (b) are block diagrams showing examples of the arrangement of basic circuits for processing sensor outputs in order to perform sensor characteristic correction for each of the sensors of the apparatus of FIG. 1.
Figure 16B:
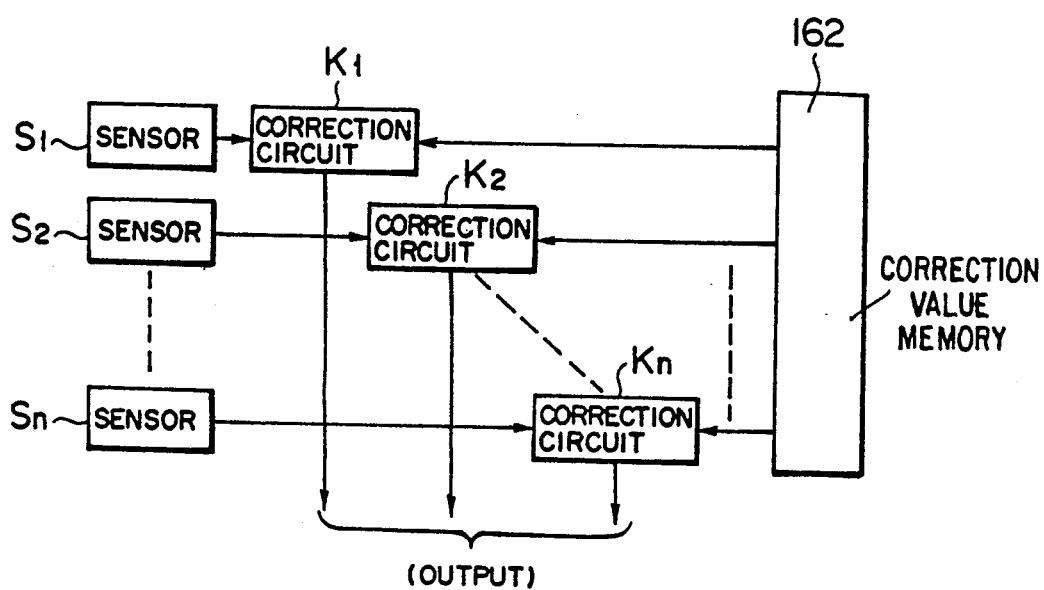

FIGS. 16 (a) and (b) show circuits which enable output measurement values to be corrected to the newest correction values even during an operation of the apparatus. Shown in these figures are examples of the arrangement of basic circuits for correcting the output of each sensor at any time desired and within a short period of time. The circuit shown in FIG. 16 (a) is used to calculate correction values for correcting the sensor outputs, and the circuit shown in FIG. 16 (b) is used to output corrected sensor outputs. In these figures, it is assumed that sensors $S_1, S_2, \ldots S_n$ correspond to the light receives $R_1$ to $R_{32}$ shown in FIG. 1 that are arranged in a row extending vertically of the associated tank 10, and disposed as shown in FIG. 3 in relation to the light emitters $L_1$ to $L_{16}$.

The arithmetic and control unit 21 of the apparatus 20 includes the elements of the circuits shown in FIGS. 16 (a) and 16 (b), namely, a mean value calculation circuit 161, a correction value memory 162, comparators $C_1, C_2, \ldots C_n$, and correction circuits $K_1, K_2, \ldots K_n$.

The mean value calculation circuit 161 inputs the outputs of the sensors $S_1$ to $S_n$, calculates the mean of the sensor outputs, and sends the calculated mean value to each of the comparators $C_1$ to $C_n$.

Each of the comparators $C_1$ to $C_n$ inputs the output of one of the sensors, compares the sensor output with the mean value supplied from the mean value calculation circuit 161. If the ratio between the compared sensor output and the mean value exceeds a predetermined ratio, the comparator calculates a value with which the output of the particular sensor should be corrected, then sends the calculated value to the correction value memory 162.

The correction value memory 162 stores sensor output correction values each corresponding to one of the sensors $S_1$ to $S_n$. The stored correction values are thus prepared for the correction of the next outputs of the sensors.

When the sensors $S_1$ to $S_n$ generate the next outputs, the correction circuits $K_1$ to $K_n$ input these outputs, read the corresponding correction values, correct the sensor outputs with the read correction values, and output the corrected sensor outputs.

The above-described calculation and storing of correction values by the system shown in FIG. 16 (a) and the correction of sensor outputs by the system shown in FIG. 16 (b) are performed within a very short period of time by, in the case of the apparatus shown in FIG. 1, controlling the mean value calculation circuit 161, the correction value memory 162, the comparators $C_1$ to $C_n$, and the correction circuit $K_1$ to $K_n$ by a controller (not shown) in the ACU 21.

The correction values stored in the correction value memory 162 in correspondence with the sensors are updated either by an operation performed from the outside of the apparatus at an arbitrarily set time such as a time before the start of a series of measurements, or by an automatic and periodically-repeated operation performed within a very short period of time during an operation of the apparatus. Alternatively, the updating may be performed by both operations.

Figure 17:
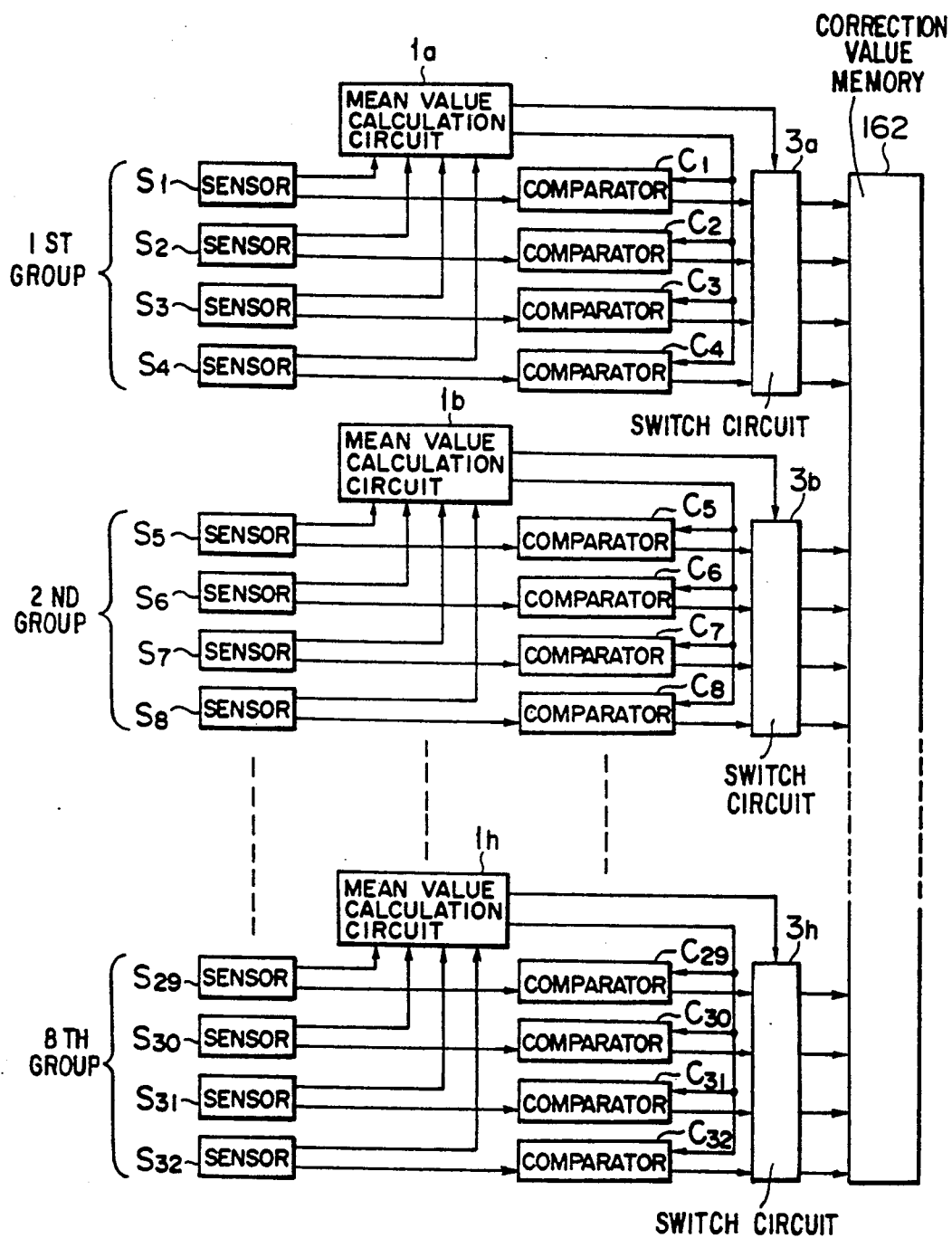
FIG. 17 is a block diagram showing an example of the arrangement of a circuit for calculating correction values, which circuit is an example of the application of the circuit shown in FIG. 16 (a)

FIG. 17 shows an example of the arrangement of a circuit for calculating correction values for sensors, which circuit is an application of the circuit shown in FIG. 16 (a) to the resin particle distinguishing apparatus 20 shown in FIGS. 1 to 4.

In FIG. 17, a first group of sensors $S_1, S_2, \ldots S_4$ correspond to the light receivers $R_1, R_2, \ldots R_4$ shown in FIGS. 1 and 3, and a second group of sensors $S_5, S_6, S_8$ correspond to the light receivers $R_5, R_6, \ldots R_8$. Similarly, forth to eighth groups of sensors correspond to different sets of sensors, with the eighth group of sensors $S_{29}, S_{30}, \ldots S_{32}$ corresponding to the light receivers $R_{29}, R_{30}, \ldots R_{32}$.

The light receivers $R_1$ to $R_{32}$ are disposed as shown in FIG. 3 and confront the ion exchange tank 10 which, during operation, usually contains anions 11 and cations 12 in water or another liquid 13. Accordingly, the regions which the individual light receivers confront vary one from another, and comprise regions solely occupied by water, regions solely occupied by anions, regions solely occupied by cations, etc. In this condition, it is meaningless to obtain the mean value of all the output values from the light receivers $R_1$ to $R_{32}$. For this reason, as shown in FIG. 17, the outputs of the sensors are divided into a plurality of groups (in the illustrated example, each group comprising four sensor outputs), which sensor output groups are individually processed to calculate correction values.

The system shown in FIG. 17 processes a first group of sensor outputs in the following manner. A mean value calculation circuit 1a calculates the mean value of the outputs of the sensors $S_1$ to $S_4$, and sends the calculated mean value to comparators $C_1$ to $C_4$ as well as to a switch circuit 3a. Each of the comparators $C_1$ to $C_4$ compares the output of the corresponding one of the sensors $S_1$ to $S_4$ with the sent mean value, and, if the ratio between the compared output and the mean value is above a predetermined ratio, the comparator calculates a value with which the output of the particular sensor should be corrected, then sends the correction value to a correction value memory 162 via the switch circuit 3a.

The switch circuit 3a operates in such a manner that, when the mean value supplied from the mean value calculation circuit 1a is determined to represent output values which contain a boundary-determining change in the reflective characteristic of the subject of measurement in the region confronting the sensors $S_1$ to $S_4$ (i.e., which indicate the existence of a boundary in this region between, e.g., anions and cations), prohibits the inputting of data from the comparators $C_1$ to $C_4$. On the other hand; when the mean value supplied from the mean value calculation circuit 1a is determined to represent output values which do not contain such a boundary-determining change (i.e., which indicate that the pertinent region is solely occupied by water, anions or cations), the switch circuit 3a permits the data from the comparators $C_1$ to $C_4$ to pass therethrough to be sent to the memory 162.

Each of second to eighth sensor output groups is processed in a similar manner, whereby, only when the sensor outputs are determined to contain no boundary-determining change in the reflective characteristic of the subject, the values with which the sensor outputs should be corrected are sent to the correction value memory 162 so as to record them or update the already-stored records.

In this way, correction values for correcting the outputs of the individual sensors are recorded in the correction value memory 162.

An operation of the apparatus involves frequent changes in the state of the subject of measurement confronting the groups of sensors, hence, in the characteristic thereof. Therefore, the contents of the correction value memory 162 concerning only those sensors whose outputs do not contain any boundary-determining change in the characteristic make it possible to always supply new data to the sensors. In addition, it is possible to prevent the correction values from being updated to erroneous values.

Figure 18:
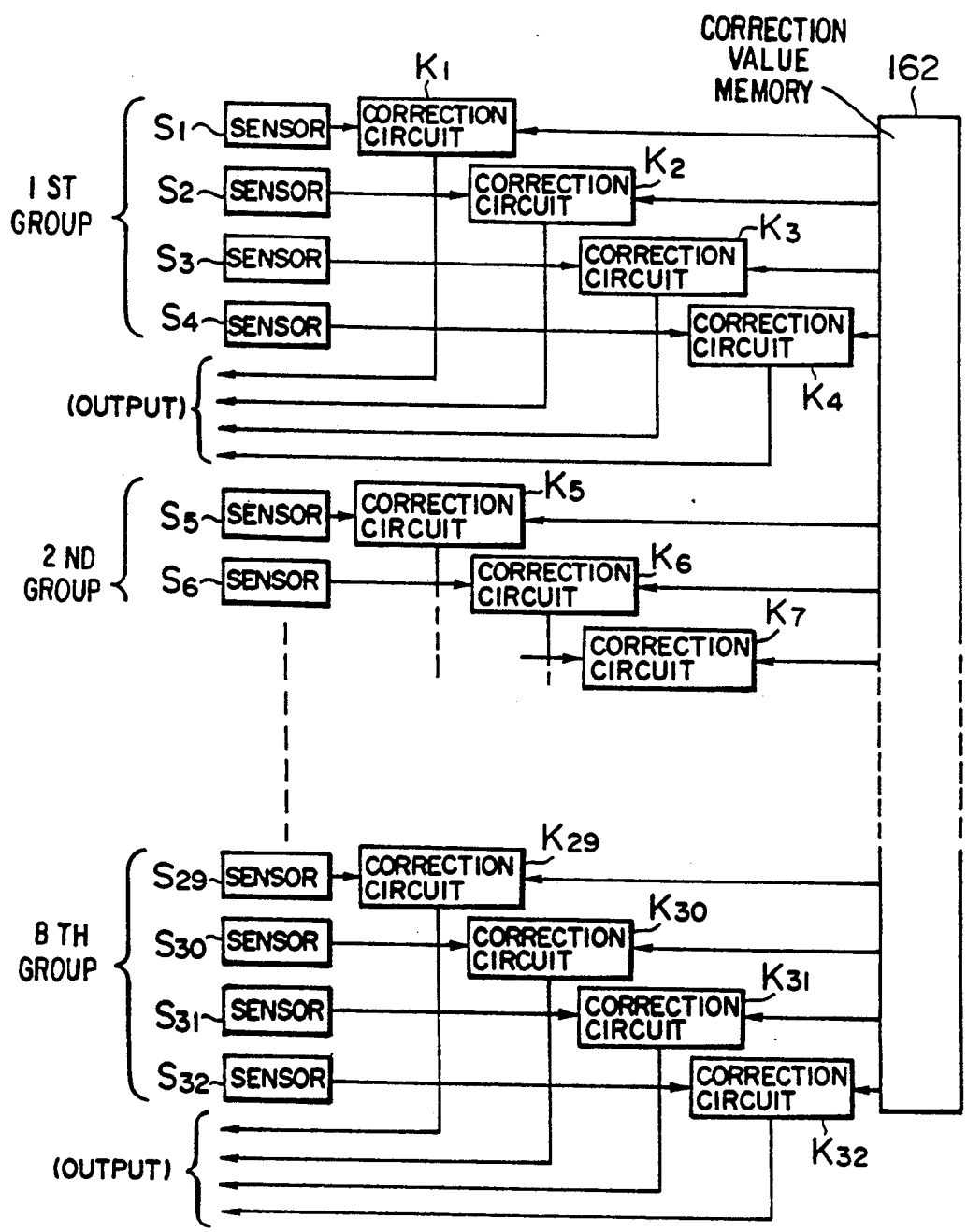
FIG. 18 is a block diagram corresponding to FIG. 17, showing a circuit for correcting sensor outputs, which circuit is an example of the application of the circuit shown in FIG. 16 (b)

FIG. 18 is a view corresponding to FIG. 17, showing an example of the arrangement of a sensor output correcting circuit, which circuit is an application of the circuit shown in FIG. 16 (b) to the resin particle distinguishing apparatus 20 shown in FIGS. 1 to 4.

In FIG. 18, sensors $S_1$ to $S_{32}$, divided into first to eighth groups, and a correction value memory 162 are the same elements that are shown in FIG. 17, and they respectively correspond to the sensors $S_1$ to $S_n$ and the correction value memory 162 shown in FIG. 16 (b). Correction circuits $K_1$ to $K_{32}$ correspond to the correction circuits $K_1$ to $K_n$ shown in FIG. 16, and their operation, which is the same as the operation of $K_1$ to $K_n$, will not be described in order to avoid redundancy.

Even with the circuit arrangement shown in FIG. 17, when the sensor outputs greatly vary from one another and are thus distorted for some reason or other, the reliability of the obtained correction values is degraded greatly. In such cases, the sensor outputs should be output as they are uncorrected rather than corrected by the circuit shown in FIG. 18 because, with uncorrected outputs, it is possible to directly observe the situation, thereby making it easier to detect the cause of the distortion.

Figure 19:
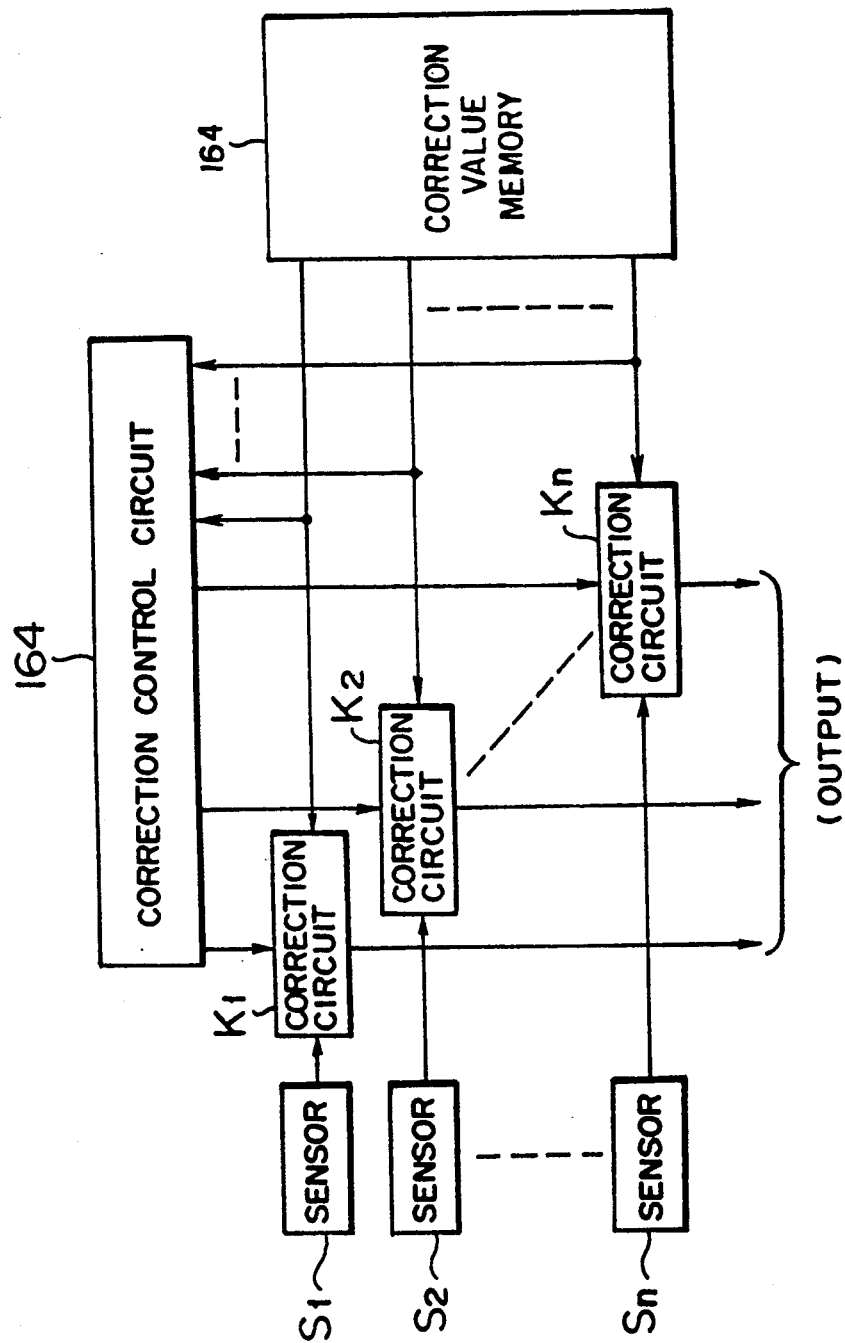
FIG. 19 is a block diagram showing a further example of a sensor output correcting circuit in which a correction control circuit is added to the basic circuit shown in FIG. 16 (b).

FIG. 19 shows the arrangement of a correction system featuring a circuit for prohibiting correction when the reliability of the contents of the correction value memory is degraded. The circuit arrangement shown in FIG. 19 differs from that shown in FIG. 16 (b) in that the former includes a correction control circuit 164 for stopping the correction operation of correction circuits $K_1$ to $K_n$ when the ratio of the number of the sensor outputs which must be corrected to the total of the sensor outputs is above a predetermined ratio.

In this system, the correction control circuit 164 inputs the sensor-output-corresponding correction values read from the correction value memory 162, calculates the number of sensor outputs requiring correction, calculates the ratio of the number of these particular sensor outputs to the total of the sensor outputs, and, if this ratio exceeds a predetermined ratio, outputs a correction stop signal simultaneously to all of the correction circuits $K_1$ to $K_n$. Upon receiving the correction stop signal, the correction circuits $K_1$ to $K_n$ output the corresponding sensor outputs as they are, uncorrected, whether or not there are inputs from the correction memory 162.

The supply of a correction signal to the correction circuits may not be simultaneous and directed to all of the correction circuits. Alternatively, a correction signal may be output to only those correction circuits to which correction values are input from the memory 162, and by which correction-requiring sensor outputs are received.

Further, the correction control circuit 164 may alternatively be incorporated in a controller for performing other control in general.

Still further, a correction control 164 such as that shown in FIG. 19 may be provided in a system such as that shown in FIG. 18, for processing sensor outputs divided into groups, so that, when sensor outputs are greatly distorted, correction is prohibited.

As has been described above, with a method and an apparatus for distinguishing particles in a liquid according to the present invention, it is possible to distinguish the individual existence of first and second groups of particles which are contained in a liquid and are different in characteristics from each other.

When the method and the apparatus are adopted as a method and an apparatus for distinguishing ion exchange resins, clear distinguishing between the resins is possible even when particles of the resins are old and have already adsorbed clad, etc., by projecting a plurality of beams comprising different wavelength bands onto the subject of measurement, measuring the reflectivities of the beam reflected by the subject, and making determinations utilizing the fact that anions and cations have different reflective characteristics with respect to light having different wavelengths. The method and the apparatus are advantageous in that they are capable of individual identification of the resin particles, which is not a comparative distinguishing.

Light-receiving elements for measuring the reflective characteristics of the subject are provided as arranged in a row extending vertically of a transparent window of the associated ion exchange tank. This arrangement makes it possible to detect the position of a boundary between a portion of the subject which is solely occupied by the liquid and a portion of the same which is occupied by the ion exchange resins, as well as the position of a boundary between anions and cations. Therefore, it is possible to correctly and easily perform an automatized ion exchange operation.

If a means is provided for calibrating sensitivity degrees and color standards for each of the beams to be used, it is possible to correct variations in the characteristics of the reflectivity measuring elements as well as changes in the same characteristics with the passage of time, thereby enabling correct determination.

If light-emitting elements for measuring the reflectivities are disposed in such a manner that the light emitted from the light-emitting elements in the main radiation direction is obliquely incident upon the surface of the transparent window of the tank, it is possible to prevent the light reflected from the transparent window from entering the light-receiving elements, hence, to prevent great errors in the measurement. Therefore, it is possible to effect error-free correct determination.

When the apparatus is mounted on, for instance, the ion exchange tank, the main body of the apparatus is accommodated in a tightly-sealed structure, thereby preventing the risk that the transparent window of the tank may be stained with water drops or be fogged by dew, hence, preventing the risk of a stained or fogged window causing errors in the measurement of reflectivities. Therefore, it is always possible to obtain correct measurement results.

According to the present invention, measurement outputs of the apparatus are processed by either (1) weighting measurement values output from mutually adjacent sensors, then averaging the weighted values; or (2) calculating a plurality of simple means, and further averaging the simple means, thereby obtaining the same result as that obtained by weighted mean calculation. The resultant mean values are compared with one another for determination. This processing makes it possible to reduce the influence of anomalous measurement values due to variations in the sensor characteristics or contamination of the subject, hence, to assure correct determination.

Prior to the determination, certain procedures are executed wherein the measurement values of the sensors are divided into several group each comprising data from mutually adjacent sensors, the mean values of the groups are compared with one another, and each of the groups is examined to see whether the group contains a boundary-determining value, thereby making a rough estimation of the position of the boundary. If the number of the items of data belonging to one group is decreased from a large value adopted in the first stage to smaller values successively adopted in the second and the following stages, it is possible to successively narrow the range possibly containing data indicating the position of a boundary. In this way, it is possible to simplify the processes starting with the inputting of data and ending in the determination of boundary positions, hence, to greatly reduce the required time.

In order to individually correct the characteristics of the sensors of the apparatus according to the present invention, the mean value of the measurement outputs of mutually adjacent sensors is compared with each of the measurement values used to obtain the mean value, and, if the ratio between the compared values is within a predetermined range, correction values are calculated from the mean values and the individual output values, and the outputs of the individual sensors are corrected using the correction value. This correction eliminates the need of preparing a reference reflecting surface and the like for the optical sensors. Therefore it is possible to easily obtain correction values for the individual sensor outputs within a short time during operation and without hindering measurement.

Further, the sensor outputs are divided into a plurality of groups each comprising mutually adjacent sensor outputs, and only when a group of sensor outputs indicates change-lacking characteristics of the subject in the region confronting the sensors, correction values are calculated, and the record in a correction memory is updated with the correction values. This updating enables correction of sensor outputs with correction values which are always correct, and enables exclusion of erroneous correction values.

Still further, when the ratio of the number of those sensor outputs which must be corrected to the total sensor outputs is above a predetermined ratio, the sensor output correction is prohibited, and the sensor outputs involving such an abnormality are output without correction, which may be then displayed. In this way, the abnormal situation can be easily and correctly recognized.

What is claimed is:

1. A method of determining the individual existence of a first group of particles contained in a fluid and a second group of particles in the same fluid but with characteristics different from the first particles that is capable of distinguishing particles in a fluid, the method comprising:

determining the position of a boundary that is indicated by a change in characteristic value by using a plurality of sensors, the step of determining the position including the steps of
     for each of a sequence of groupings of mutually adjacent sensors among all the sensors, effecting a predetermined weighting of each of the measurement values output from the sensors of the respective grouping,
     obtaining weighted means for each of the groupings of mutually adjacent sensors from the weighted measurement values, and
     comparing the weighted means with one another to detect the first and second groups of particles.

2. A method for determining particles in a fluid according to claim 1, wherein the groupings in the sequence include a subset of groupings each containing sensors which are not contained in any other groupings in the subset, and wherein the step of determining the position further comprises the steps of: for each grouping in the subset, calculating the mean value of the measurement values output from the sensors of the respective grouping to provide a calculated mean value; and examining the calculated mean values to check whether or not there is any in grouping or inter--grouping change indicating the position of a boundary between the first and second groups of particles or between either group of particles and the fluid.

3. A method for distinguishing particles in a fluid according to claim 2, wherein a range possibly containing a change indicating the position of a boundary is successively narrowed by dividing the sensors of the respective grouping into a plurality of smaller groupings, comparing the mean values of the measurement values of the smaller groupings with one another, and repeating the aforesaid steps a plurality of times in such a manner that, each time the steps are executed, the number of sensors belonging to one grouping is different, the number of sensors being largest in the first execution of the steps and thereafter decreasing in a plurality of successive stages.

4. A method of determining the individual existence of a first group of particles contained in a fluid and a second group of particles in the same fluid but with characteristics different from the first particles that is capable of distinguishing particles in a fluid, the method comprising:

determining the position of a boundary that is indicated by a change in characteristic value by using a plurality of sensors, the step of determining the position including the steps of
     obtaining a sequence of first mean values by conducting, for each of a sequence of groupings of mutually adjacent sensors among all the sensors, an averaging of the measurement values output from the mutually adjacent sensors of the respective grouping,
     obtaining a sequence of second mean values by conducting, for each of a sequence of groupings of first mean values, an averaging of the first mean values of the respective grouping of first mean values,
     repeating the aforesaid averaging if necessary until a sequence of nth mean values (n being an integer at least equal to two) is obtained, and
     comparing the nth mean values with one another to detect the first and second groups of particles.

5. A method for determining particles in a fluid according to claim 4, wherein the groupings in the sequence include a subset of groupings each containing sensors which are not contained in any other grouping in the subset, and wherein the step of determining the position further comprises the steps of: for each grouping in the subset, calculating the mean value of the measurement values output from the sensors of the respective grouping to provide a calculated mean value; and examining the calculated mean values to check whether or not there is any in-grouping or inter-grouping change indicating the position of the boundary between the first and second groups of particles or between either group of particles and the fluid.

6. A method for distinguishing particles in a fluid according to claim 5, wherein a range possibly containing a change indicating the position of a boundary is successively narrowed by dividing the sensors of the respective grouping into a plurality of smaller groupings, comparing the mean values of the measurement values of the smaller groups with one another, and repeating the aforesaid steps a plurality of times in such a manner that, each time the steps are executed, the number sensors belonging to one grouping is different, the number of sensors belonging to one grouping being largest in the first execution of the steps and thereafter decreasing in a plurality of successive stages.

7. A method of determining the individual existence of a first group of particles contained in a fluid and a second group of particles in the same fluid but with characteristics different from the first particles that is capable of distinguishing particles in a fluid, the method comprising:

determining the position of a boundary that is indicated by a change in characteristic value by using a Plurality of sensors, the step of determining the position including the steps of
     obtaining a sequence of first weighted mean values by conducting, for each of a sequence of groupings of mutually adjacent sensors among all the sensors, a predetermined weighting of and then an averaging of measurement values output from the mutually adjacent sensors of the respective grouping,
     obtaining a sequence of second weighted mean values by conducting, for each of a sequence of groupings of adjacent first weighted mean values, a different weighting of and then an averaging of the first weighted mean values of the respective grouping of first weighted mean values, repeating the aforesaid steps if necessary until a sequence of mth weighted mean values (m being an integer at least equal to two) is obtained, and comparing the mth weighted mean values with one another to detect the first and second groups of particles.

8. A method for determining particles in a fluid according to claim 7, wherein the groupings in the sequence include a subset of groupings each containing sensors which are not contained in any other grouping in the subset, and wherein the step of determining the position further comprises the steps of: for each grouping in the subset, calculating the mean value of the measurement values output from the sensors of the respective grouping to provide a calculated mean value; and examining the calculated mean values to check whether or not there is any in-grouping or inter-grouping change indicating the position of a boundary between the first and second groups of particles or between either group of particles and the fluid.

9. A method for distinguishing particles in a fluid according to claim 8, wherein a range possibly containing a change indicating the position of a boundary is successively narrowed by dividing the sensors of the respective grouping into a plurality of smaller groups, comparing the mean values of the measurement values of the smaller groupings with one another, and repeating the aforesaid steps a plurality of times in such a manner that, each time the steps are executed, the number of sensors belonging to one grouping is different, the number of sensors belonging to one grouping being largest in the first execution of the steps and thereafter decreasing in a plurality of successive stages.

10. A method of determining the individual existence of a first group of particles contained in a fluid and a second group of particles in the same fluid but with characteristics different from the first particles that is capable of distinguishing particles in a fluid, the method comprising the steps of:
determining the mean value of measurement values produced by sensors in a group of mutually adjacent sensors;
comparing the mean value with each of the measurement values used to obtain the mean value;
if a ratio expressing the result of the comparison falls outside a predetermined range, determining that there is an error in the characteristics of the sensor which produced the particular measurement value;
calculating, on the basis of both the measurement value of the sensor determined to be erroneous and the mean value, a value with which the particular measurement value should be corrected;
storing the calculated value as a correction value in a memory; and
effecting the subsequent measurements in such a manner that the measurement values output from the sensor determined to be erroneous are corrected using the correction value stored in the memory.

11. A method for distinguishing particles in a fluid according to claim 10, wherein the group of sensors is one of a plurality of groups of mutually adjacent sensors, and wherein the method further comprising the steps of: analyzing the measurement values produced by the sensors of all the groups to determine whether any of these groups contains sensors which sense a boundary-determining change in characteristic value; and subjecting only those groups which are determined to contain no sensors which sense a boundary-determining change to an updating of correction values for correcting the measurement values belonging to these groups.

12. A method for distinguishing particles in a fluid according to claim 10, wherein the number of sensors which have their measurement values corrected with correction values is limited in such a manner that the ratio of the number of these sensors to the total of the sensors is below a predetermined value.

13. A method for distinguishing particles in a fluid according to claim 11, wherein the number of sensors which have their measurement values corrected with correction values is limited in such a manner that the ratio of the number of these sensors to the total of the sensors is below a predetermined value.

14. A method of determining the individual existence of a first group of particles contained in a fluid and a second group of particles in the same fluid but with characteristics different from the first particles that is capable of distinguishing particles in a fluid, the method comprising:
determining the position of a boundary that is indicated by a change of characteristic value by using a plurality of sensors, the step of determining the position including the steps of
dividing the sensors into a sequence of groupings, each grouping having a plurality of sensors and each sensor belonging to only one of the groupings,
for each grouping of sensors, calculating the mean value of measurement values produced by the sensors of the respective grouping,
examining the mean values in order to divide the groupings into at least three sets, the at least three sets including a first set for groupings whose sensors are definitely exposed to only the first group of particles, a second set of groupings whose sensors are definitely exposed to only the second group of particles, and a third set for uncertain groupings whose sensors are exposed to a region that may include a boundary between the first and second groups of particles, and
conducting further examination of the measurement values of some of the sensors, including at least the sensors in the third set, to find at least one sensor in the third set that is definitely exposed to particles or the first group of particles of the second group.

15. The method of claim 14, wherein each grouping includes a predetermined number of sensors, and wherein the step of conducting further examination comprises:
dividing the sensors in the third set into a sequence of further groupings, each further grouping having fewer sensors than the predetermined number and each sensor in a further grouping belonging to no other further grouping,
for each further grouping of sensors, calculating the mean value of measurement values produced by sensors of the respective further grouping, and
examining the mean values in order to divide the further groupings into at least three further sets, the at least three further sets including a first further set for further groupings whose sensors are definitely exposed to only the first group of particles, a second further set for further groupings whose sensors are definitely exposed to only the second group of particles, and a third further set for uncertain further groupings whose sensors are exposed to a region that may include a boundary between the first and second groups of particles.

16. The method of claim 15, further comprising conducting further examination of the measurement values of some of the sensors, including at least the sensors in the further uncertain set, to find at least one sensor in the further uncertain set that is definitely exposed to particles of the first group or particles of the second group.

* * * * *